US007994129B2

(12) United States Patent
Donahue

(10) Patent No.: US 7,994,129 B2
(45) Date of Patent: Aug. 9, 2011

(54) METHODS OF USING BLACK BEAR PARATHYROID HORMONE

(75) Inventor: Seth W. Donahue, Houghton, MI (US)

(73) Assignee: Michigan Technological University, Houghton, MI (US)

( * ) Notice: Subject to any disclaimer, the term of this patent is extended or adjusted under 35 U.S.C. 154(b) by 0 days.

(21) Appl. No.: 11/559,285

(22) Filed: Nov. 13, 2006

(65) Prior Publication Data

US 2007/0219132 A1 Sep. 20, 2007

Related U.S. Application Data

(60) Provisional application No. 60/736,145, filed on Nov. 10, 2005.

(51) Int. Cl.
*A61K 38/00* (2006.01)
*A61K 38/29* (2006.01)

(52) U.S. Cl. ............... 514/11.8; 514/16.7; 514/16.8; 514/16.9; 514/17.1

(58) Field of Classification Search ............... None
See application file for complete search history.

(56) References Cited

U.S. PATENT DOCUMENTS

| | | | |
|---|---|---|---|
| 4,086,196 A | 4/1978 | Tregear | |
| 4,698,328 A | 10/1987 | Neer et al. | |
| 4,812,304 A | 3/1989 | Anderson et al. | |
| 4,822,609 A | 4/1989 | Flora | |
| 5,118,667 A | 6/1992 | Adams et al. | |
| 5,164,368 A | 11/1992 | Recker | |
| 5,208,041 A | 5/1993 | Sindrey | |
| 5,317,010 A | 5/1994 | Pang et al. | |
| 5,457,092 A | 10/1995 | Schluter et al. | |
| 5,496,801 A | 3/1996 | Holthuis et al. | |
| 5,510,370 A | 4/1996 | Hock | |
| 5,556,940 A | 9/1996 | Willick et al. | |
| 5,578,567 A | 11/1996 | Cardinaux et al. | |
| 5,589,452 A | 12/1996 | Krstenansky et al. | |
| 5,607,915 A | 3/1997 | Patton | |
| 5,616,560 A | 4/1997 | Geddes et al. | |
| 5,723,577 A | 3/1998 | Dong | |
| 5,744,444 A | 4/1998 | Forssmann et al. | |
| 5,747,456 A | 5/1998 | Chorev et al. | |
| 5,783,558 A | 7/1998 | Duvos et al. | |
| 5,807,823 A | 9/1998 | Krstenansky et al. | |
| 5,814,607 A | 9/1998 | Patton | |
| 5,821,225 A | 10/1998 | Vickery | |
| 5,874,086 A | 2/1999 | Krstenansky et al. | |
| 5,955,425 A | 9/1999 | Morley et al. | |
| 5,977,070 A | 11/1999 | Piazza et al. | |
| 6,025,467 A | 2/2000 | Fukuda et al. | |
| 6,080,721 A | 6/2000 | Patton | |
| 6,110,892 A | 8/2000 | Barbier et al. | |
| 6,284,730 B1 | 9/2001 | Dietrich et al. | |
| 6,316,410 B1 | 11/2001 | Barbier et al. | |
| 6,436,902 B1 | 8/2002 | Backstrom et al. | |
| 6,495,662 B1 | 12/2002 | Gardella et al. | |
| 6,500,647 B1 | 12/2002 | Jung et al. | |
| 6,526,316 B2 * | 2/2003 | Iga et al. ............... 604/20 |
| 6,583,114 B2 | 6/2003 | Vickery | |
| 6,590,081 B1 | 7/2003 | Zhang | |
| 6,756,480 B2 | 6/2004 | Kostenuik et al. | |
| 6,770,623 B1 | 8/2004 | Chang et al. | |
| 6,849,710 B1 | 2/2005 | Arzeno | |
| 6,855,337 B1 | 2/2005 | Nelson et al. | |
| 6,923,968 B2 | 8/2005 | Cantor | |
| 6,977,077 B1 | 12/2005 | Hock et al. | |
| 7,015,195 B2 | 3/2006 | Stewart | |
| 7,018,982 B2 | 3/2006 | Dietrich et al. | |
| 2002/0002135 A1 | 1/2002 | Dietrich et al. | |
| 2002/0025929 A1 | 2/2002 | Sato | |
| 2002/0094951 A1 | 7/2002 | Horiuchi et al. | |
| 2002/0132973 A1 | 9/2002 | Condon et al. | |
| 2002/0136779 A1 | 9/2002 | Lehmann | |
| 2003/0087822 A1 | 5/2003 | Cantor | |
| 2003/0171282 A1 | 9/2003 | Patton | |
| 2004/0005668 A1 | 1/2004 | Gautvik et al. | |
| 2004/0023882 A1 | 2/2004 | Peri et al. | |
| 2004/0033950 A1 | 2/2004 | Hock et al. | |
| 2004/0186050 A1 | 9/2004 | Ault et al. | |
| 2004/0209851 A1 | 10/2004 | Nelson et al. | |

(Continued)

FOREIGN PATENT DOCUMENTS

| | | |
|---|---|---|
| CN | 1712066 | 12/2005 |
| EP | 0341963 | 11/1989 |
| EP | 0490806 | 6/1992 |
| EP | 1417972 | 5/2004 |
| FR | 2666987 | 3/1992 |

(Continued)

OTHER PUBLICATIONS

Rosol et al., 1995, Gene 160:241-243.*
Akamine, T. et al., "Prostaglandin E2 prevents bone loss and adds extra bone to immobilized distal femoral metaphysis in femal rats," Bone (1992) 13:11-22.
Altschul, S.F. et al., "Gapped BLAST and PSI-BLAST: a new generation of protein database search programs," Nuc. Acids Res. (1997) 25:3389-3402.
Arnaud, S.B. et al., "Effects of 1-week head-down tilt bed rest on bone formation and the calcium endocrine system," Aviat. Space Environ. Med. (1992) 63:14-20.

(Continued)

*Primary Examiner* — Elizabeth C Kemmerer
(74) *Attorney, Agent, or Firm* — Michael Best & Friedrich LLP

(57) ABSTRACT

Black bear parathyroid hormone (PTH) and functional fragments thereof are provided. Also provided are methods of using black bear PTH and functional fragments for increasing cAMP in a bone-forming cell; reducing apoptosis in a bone-forming cell; decreasing the ratio of expression levels of Bax protein to Bcl-2 protein in a bone-forming cell; increasing the expression level of one or more of a bone matrix protein, a transcriptional activator, or a transcriptional regulator in a bone-forming cell; enhancing bone mineral density, increasing bone mass, decreasing bone loss, or reducing the incidence of bone fractures, or any combination thereof, in a subject; also provided are antibodies directed against black bear parathyroid hormone (PTH) and functional fragments thereof.

18 Claims, 7 Drawing Sheets

U.S. PATENT DOCUMENTS

| | | |
|---|---|---|
| 2004/0242478 A1 | 12/2004 | Azria et al. |
| 2004/0242489 A1 | 12/2004 | Mitlak |
| 2005/0009147 A1 | 1/2005 | Bauer et al. |
| 2005/0032685 A1 | 2/2005 | Noda |
| 2005/0032698 A1 | 2/2005 | Day et al. |
| 2005/0037089 A1 | 2/2005 | Jobbins |
| 2005/0054557 A1 | 3/2005 | Goldberg |
| 2005/0095236 A1 | 5/2005 | Zahradnik et al. |
| 2005/0107292 A1 | 5/2005 | Minamitake et al. |
| 2005/0119183 A1 | 6/2005 | Wells et al. |
| 2005/0148763 A1 | 7/2005 | Sekimori et al. |
| 2005/0192227 A1 | 9/2005 | Hock |
| 2005/0197294 A1 | 9/2005 | Gaich et al. |
| 2005/0209144 A1 | 9/2005 | Billger et al. |
| 2005/0215476 A1 | 9/2005 | Mehta et al. |
| 2005/0255537 A1 | 11/2005 | Hock et al. |
| 2005/0256045 A1 | 11/2005 | Ameri et al. |
| 2005/0272660 A1 | 12/2005 | Gardella et al. |
| 2005/0276843 A1 | 12/2005 | Quay et al. |
| 2006/0019902 A1 | 1/2006 | Caporale et al. |
| 2006/0052305 A1 | 3/2006 | Quay et al. |
| 2006/0058230 A1 | 3/2006 | Chorev et al. |
| 2006/0069021 A1 | 3/2006 | Costantino et al. |
| 2006/0089723 A1 | 4/2006 | Murphy |
| 2006/0094642 A1 | 5/2006 | Gaich et al. |
| 2006/0127320 A1 | 6/2006 | Costantino et al. |

FOREIGN PATENT DOCUMENTS

| | | |
|---|---|---|
| JP | 2006143603 | 6/2006 |
| WO | WO 93/06846 | 4/1993 |
| WO | WO 94/03201 | 2/1994 |
| WO | WO 95/02610 | 1/1995 |
| WO | WO 96/07416 | 3/1996 |
| WO | WO 96/07417 | 3/1996 |
| WO | WO 96/07418 | 3/1996 |
| WO | WO 96/19246 | 6/1996 |
| WO | WO 96/35447 | 11/1996 |
| WO | WO 98/30590 | 7/1998 |
| WO | WO 00/19823 | 4/2000 |
| WO | WO 01/23521 | 4/2001 |
| WO | WO 01/32201 | 5/2001 |
| WO | WO 2004/024758 | 3/2004 |
| WO | WO 2004/060386 | 7/2004 |
| WO | WO 2004/085562 | 10/2004 |
| WO | WO 2005/002549 | 1/2005 |
| WO | WO 2006/006674 | 1/2006 |
| WO | WO 2006/033912 | 3/2006 |
| WO | WO 2007/059470 | 5/2007 |

OTHER PUBLICATIONS

Bakker, A.D. et al., "Interactive effects of PTH and mechanical stress on nitric oxide and PGE2 production by primary mouse osteoblastic cells," Am. J. Physiol. Endocrinol. Metab. (2003) 285:E608-E613.
Bellido, T. et al., "Chronic elevation of parathyroid hormone in mice reduces expression of sclerostin by osteocytes: a novel mechanism for hormonal control of osteoblastogenesis," Endocrinology (2005) 146:4577-4583.
Bellido, T. et al., "Proteasomal degradation of Runx2 shortens parathyroid hormone-induced anti-apoptotic signaling in osteoblasts," J. Biol. Chem. (2003) 278(50):50259-50272.
Berg, C. et al., "Teriparatide," Nature Reviews Drug Discovery (2003) 2:257-258.
Bikle, D.D. et al, "The impact of skeletal unloading on bone formation," Gravit Space Biol. Bull. (2003) 16:45-54.
Bikle, D.D. et al., "Insulin-like growth factor I is required for the anabolic actions of parathyroid hormone on mouse bone," J. Bone Miner. Res. (2002) 17:1570-1578.
Bikle, D.D. et al., "Skeletal unloading induces resistance to insulin-like growth factor I," J. Bone Min. Res. (1994) 9:1789-1796.
Bringhurst, F.R. et al., "Peripheral metabolism of PTH: fate of biologically active amino terminus in vivo," Am. J. Physio. (1988) 255:E886-E893.
Burge, R.T. et al., "Methodology for estimating current and future burden of osteoporosis in state populations: application to Florida in 2000 through 2025," Value in Health (2003) 6:574-583.
Burguera, B. et al., "Leptin reduces ovariectomy-induced bone loss in rats," Endocrinology (2001) 142:3546-3553.
Canalis, E. et al., "Insulin-like growth factor I mediates selective anabolic effects of parathyroid hormone in bone cultures," J. Clin. Invest. (1989) 83:60-65.
Carmeliet, G. et al., "Gene expression related to the differentiation of osteoblastic cells is altered by microgravity," Bone (1998) 22:139S-143S.
Carter, P.H. et al., "The hydrophobic residues phenylalanine 184 and leucine 187 in the type-I parathyroid hormone (PTH) receptor functionally interact with the amino-terminal portion of PTH-(1-34)," J. Biol. Chem. (1999) 274(45):31955-31960.
Chen, X. et al., "Termination of immediate-early gene expression after stimulation by parathyroid hormone or isoproterenol," Am. J. Physiol. Cell Physiol. (2002) 283(5):C1432-C1440.
Chenna, R. et al., "Multiple sequence alignment with the Clustal series of programs," Nuc. Acids Res. (2003) 31:3497-3500.
Colombo, G. et al., "Isolation and complete amino acid sequence of osteocalcin from canine bone," J. Bone Min. Res. (1993) 8:733-743.
Cummings, S.R. et al., "Epidemiology and outcomes of osteoporotic fractures," Lancet (2002) 359:1761-1767.
Dauty, M. et al., "Supralesional and sublesional bone mineral density in spinal cord-injured patients," Bone (2000) 27:305-309.
De Bruin, E.D. et al., "Long-term changes in the tibia and radius bone mineral density following spinal cord injury," Spinal Cord (2005) 43:96-101.
Demiralp, B. et al., "Anabolic actions of parathyroid hormone during bone growth are dependent on c-fos," Endocrinology (2002) 143:4038-4047.
Divieti, P. et al., "Human PTH-(7-84) inhibits bone resorption in vitro via actions independent of the type 1 PTH/PTHrP receptor," Endocrinology (2002) 143:171-176.
Divieti, P. et al., "Receptors for the carboxyl-terminal region of pth(1-84) are highly expressed in osteocytic cells," Endocrinology (2001) 142:916-925.
Donahue, S.W. et al., "Bone formation is not impaired by hibernation (disuse) in black bears (*Ursus americanus*)," J. Exp. Biol. (2003) 206:4233-4239.
Donahue, S.W. et al., "Hibernating bears as a model for preventing disuse osteoporosis," J. Biomech. (2005) Jun. 20, 2005.
Donahue, S.W. et al., "Parathyroid hormone may maintain bone formation in hibernating black bears (*Ursus americanus*) to prevent disuse osteoporosis," J. Exp. Biol. (2006) 209:1630-1638.
Dye, L., "Good Nappers—How can people keep bones strong in old age? Bears might have the answer," ABCNews at http://abcnews.go.com/sections/SciTech/DyeHard/bears_hibernation_dyehard_0... (Jan. 14, 2004).
Elefteriou, F. et al., "Leptin regulation of bone resorption by the sympathetic nervous sytem and CART," Nature (2005) 434:514-520.
Floyd, T. et al., "Calcium and bone metabolic homeostasis in active and denning black bears (*Ursus americanus*)," Clin. Orthop. Relat. Res. (1990) 255:301-309.
Frey-Rindova, P. et al., "Bone mineral density in upper and lower extremities during 12 months after spinal cord injury measured by peripheral quantitative computed tomography," Spinal Cord (2000) 38:26-32.
Fujimori, A. et al., "Dissociation of second messenger activation by parathyroid hormone fragments in osteosarcoma cells," Endocrinology (1991) 128:3032-3039.
Gullberg, B. et al., "World-wide projections for hip fracture," Osteoporosis Int. (1997) 7:407-413.
Halloran, B.P. et al., "Regional responsiveness of the tibia to intermittent administration of parathyroid hormone as affected by skeletal unloading," J. Bone Miner. Res. (1997) 12:1068-1074.
Hamilton, S.A. et al., "A murine model for bone loss from therapeutic and space-relevant sources of radiation," J. Appl. Physiol. (2006) 101(3):789-793.
Harada, S. et al., "Control of osteoblast function and regulation of bone mass," Nature (2003) 423:349-355.
Harvey, K.B. et al., "Bending properties, porosity, and ash fraction of black bear (*Ursus americanus*) cortical bone are not comprised with aging despite annual periods of disuse," J. Biomech. (2004) 37:1513-1520.

Harvey, K.B. et al., The tensile strength of black bear (*Ursus americanus*) cortical bone is not comprised with aging despite annual periods of hibernation, J. Biomech. (2005) 38:2143-2150.

Hauschka, P.V. et al., "Osteocalcin and matrix Gla protein: vitamin K-dependent proteins in bone," Physiol. Rev. (1989) 69:990-1047.

Hellgren, E.C., "Physiology of hibernation in bears," Ursus (1998) 10:467-477.

Hilliker, S. et al., "Truncation of the amino terminus of PTH alters its anabolic activity on bone in vivo," Bone (1996) 19:469-477.

Hissa, R. et al., "Seasonal changes in fatty acids and leptin contents in the plasma of the European brown bear (*Ursus arctos arctos*)," Ann. Zool. Fennici (1998) 35:215-224.

Hock, J.M. et al., "Osteoblast apoptosis and bone turnover," J. Bone Min. Res. (2001) 16:975-984.

Hodsman, A.B. et al., "Efficacy and safety of human parathyroid hormone-(1-84) in increasing bone mineral density in postmenopausal osteoporosis," J. Clin. Endocrinol. Metab. (2003) 88:5212-5220.

Houde, J.P. et al., "Bone mineral density changes in the forearm after immobilization," Clin. Orthop. (1995) 317:199-205.

Iida-Klein, A. et al., "Anabolic action of parathyroid hormone is skeletal site specific at the tissue and cellular levels in mice," J. Bone Miner. Res. (2002) 17:808-816.

Inoue, M. et al., "Altered biochemical markers of bone turnover in humans during 120 days of bed rest," Bone (2000) 26:281-286.

Ito, T. et al., "Changes in serum concentrations of calcium and its regulating hormones during tail suspension in rats," Environ. Med. (1996) 40:43-46.

Iwamoto, J. et al., "Interventions to prevent bone loss in astronauts during space flight," Keio J. Med. (2005) 54(2):55-59.

Jee, W.S. et al., "Animal models of immobilization osteopenia," Morphologic (1999) 83(261):25-34.

Jee, W.S. et al., "Prostaglandin E2 prevents disuse-induced cortical bone loss," Bone (1992) 13:153-159.

Jee, W.S., "Integrated bone tissue physiology: anatomy and physiology," in Bone Mechanics Handbook, S.C. Cowin ed., CRC Press, Boca Raton, FL (2001) 1-34.

Jiang, D. et al., "Parathyroid hormone induction of the osteocalcin gene. Requirement for an osteoblast-specific element 1 sequence in the promoter and involvement of multiple-signaling pathways," J. Biol. Chem. (2004) 279:5329-5337.

Jiang, S.D. et al., "Osteoporosis after spinal cord injury," Osteoporosis Int. (2006) 17:180-192.

Jiang, Y. et al., "Recombinant human parathyroid hormone (1-34) (teriparatide) improves both cortical and cancellous bone structure," J. Bone Min. Res. (2003) 18(11):1932-1941.

Jilka, R.L. et al., "Increased bone formation by prevention of osteoblast apoptosis with parathyroid hormone," J. Clin. Invest. (1999) 104:439-446.

Jin, L. et al., "Crystal structure of human parathyroid hormone 1-34 at 0.9-A resolution," J. Biol. Chem. (2000) 275(35):27238-27244.

Kaneps, A.J. et al., "Changes in canine cortical and cancellous bone mechanical properties following immobilization and remobilization with exercise," Bone (1997) 21:419-423.

Kanis, J. et al., "Acute and long-term increase in fracture risk after hospitalization for stroke," Stroke (2001) 32:702-706.

Keller, H. et al., "SOST is a target gene for PTH in bone," Bone (2005) 37:148-158.

Khosla, S., "Leptin-central or peripheral to the regulation of bone metabolism?" Endocrinology (2002) 143:4161-4164.

Kodama, Y. et al., "Inhibition of bone resorption by pamidronate cannot restore normal gain in cortical bone mass strength in tail-suspended rapidly growing rats," J. Bone Miner. Res. (1997) 12:1058-1067.

Kostenuik, P.J. et al., "Skeletal unloading causes resistance of osteoprogenitor cells to parathyroid hormone and to insulin-like growth factor-I," J. Bone Min. Res. (1999) 14:21-31.

Kumar, S. et al., "MEGA3: Integrated software for molecular evolutionary genetics analysis and sequence alignment," Brief Bioinform. (2004) 5:150-163.

Lanyon, L.E. et al., "Static vs dynamic loads as an influence on bone remodelling," J. Biomech. (1984) 17:897-905.

Leblanc, A. et al., "Calcium absorption, endogenous excretion, and endocrine changes during and after long-term bed rest," Bone (1995) 16:301S-304S.

Leblanc, A.D. et al., "Bone mineral loss and recovery after 17 weeks of bed rest," J. Bone Min. Res. (1990) 5:843-850.

Li, C.Y. et al., "High-dose risedronate treatment partially preserves cancellous bone mass and microarchitecture during long-term disuse," Bone (2005) 37:287-295.

Li, C.Y. et al., "Long-term disuse osteoporosis seems less sensitive to bisphosphonate treatment than other osteoporosis," J. Bone Miner. Res. (2005) 20:117-124.

Li, M. et al., "A comparison of the anabolic effects of rat and bovine parathyroid hormone (1-34) in ovariectomized rats," J. Musculoskelet. Neuronal. Interact. (2001) 2:77-83.

Ma, Y. et al., "Parathyroid hormone and mechanical usage have a synergistic effect in rat tibial diaphyseal cortical bone," J. Bone Min. Res. (1999) 14:439-448.

MacGregor, R.R. et al., "Formation and secretion of fragments of parathormone. Identification of cleavage sites," J. Biol. Chem. (1986) 261:1929-1934.

Martin, A. et al., "Leptin modulates both resorption and formation while preventing disuse-induced bone loss in tail-suspended female rats," Endocrinology (2005) 146:3652-3659.

Martin, T.J. et al., "Osteoclast-derived activity in the coupline of bone formation to resorption,"Trends Mol. Med. (2005) 11:76-81.

Matsumoto, T. et al., "Effect of mechanical unloading and reloading on periosteal bone formation and gene expression in tail-suspended rapidly growing rats," Bone (1998) 22:89S-93S.

McCarthy, T.L. et al., "Prostaglandin E2 stimulates insulin-like growth factor I synthesis in osteoblast-enriched cultures from fetal rat bone," Endocrinology (1991) 128:2895-2900.

McCauley, L.K. et al., "Parathyroid hormone stimulates fra-2 expression in osteoblastic cells in vitro and in vivo," Endocrinology (2001) 142:1975-1981.

McCauley, L.K. et al., "Proto-oncogene c-fos is transcriptionally regulated by parathyroid hormone (PTH) and PTH-related protein in a cyclic adenosine monophosphate-dependent manner in osteoblastic cells," Endocrinology (1997) 138:5427-5433.

McGee, M.E. et al., "Cortical bone porosity, mechanical and cross-sectional properties are preserved during disuse (hibernation) and do not show loss with age in grizzly and black bear femurs," 52nd Annual Meeting of the Orthopaedic Research Society, Chicago, Il, Orthopaedic Research Society (2006) Paper 1608.

McGee, M.E. et al., "Cross-sectional and whole bone structural properties of bear femurs are not compromised by annual periods of disuse," ASME Summer Bioenegineering Conference. Vail, CO, American Society of Mechanical Engineers (2005) 2 pages.

Modlesky, C.M. et al., "Deteriorated geometric structure and strength of the midfemur in men with complete spinal cord injury," Bone (2005) 36:331-339.

Mundy, G.R., "Cellular and molecular regulation of bone turnover," Bone (1999) 24:35S-38S.

Murray, T.M. et al., "Parathyroid hormone secretion and action: evidence for discrete receptors for the carboxyl-terminal region and related biological actions of carboxyl-terminal ligands," Endo. Rev. (2005) 26:78-113.

Nance, P.W. et al., "Intravenous pamidronate attenuates bone density loss after acute spinal cord injury," Arch. Phys. Med. Rehabil. (1999) 80:243-251.

Nasu, M. et al., "Carboxyl-terminal parathyroid hormone fragments stimulate type-1 procollagen and insulin-like growth factor-binding protein-5 mRNA expression in osteoblastic UMR-106 cells," Endocr. J. (1998) 45:229-234.

National Osteoporosis Foundation, "America's Bone Health: The state of osteoporosis and low bone mass in our nation," Washington D.C.: Publisher (2002) 57 pages.

Neer, R.M. et al., "Effect of parathyroid hormone (1-34) on fractures and bone mineral density in postmenopausal women with osteoporosis," N. Eng. J. Med. (2001) 344:1434-1441.

Nelson, O.L. et al., "Evaluation of cardiac function in active and hibernating grizzly bears," J. Am. Vet. Med. Assoc. (2003) 223:1170-1175.

Nelson, R.A., "Black bears and polar bears: still metabolic marvels," Mayo Clin. Proc. (1987) 62:850-853.

Nishimoto, S.K., "A colorimetric assay specific for gamma-carboxyglutamic acid-containing proteins: its utility in protein purification procedures," Anal. Biochem. (1990) 186:273-279.

Nowak, R., "Bear bones hint at osteoporosis treatment," NewScientist.com at http://www.newscientist.com/article.ns?id=dn4421&print=true (Nov. 30, 2003) 2 pages.

NPS_Pharmaceuticals (2003). NPS Reports Positive PREOS Study Results. http://www.npsp.com/news/releasetxt.php?ReqId=471943.

Orwoll, E.S. et al., "The effect of teriparatide [human parathyroid hormone (1-34)] therapy on bone density in men with osteoporosis," J. Bone Miner. Res. (2003) 18:9-17.

Pardy, C.K. et al., "Maintenance of bone mass and architecture in denning black bears (Ursus americanus)," J. Zool. Lond. (2004) 263:359-364.

Patterson-Allen, P. et al., "A specific radioimmunoassay for osteocalcin with advantageous species crossreactivity," Anal. Biochem. (1982) 120:1-7.

Pedersen, B.J. et al., "Changes in the carboxyl-terminal propeptide of type I procollagen and other markers of bone formation upon five days of bed rest," Bone (1995) 17:91-95.

Pitsillides, A.A. et al., "Mechanical strain-induced NO production by bone cells: a possible role in adaptive bone (re)modeling?" FASEB J. (1995) 9:1614-1622.

Plotkin, L.I. et al., "Mechanical stimulation prevents osteocyte apoptosis: requirement of integrins, Src kinases, and ERKs," Am. J. Physiol. Cell Physiol. (2005) 289:C633-C643.

Poole, K.E. et al., "Parathyroid hormone—a bone anabolic and catabolic agent," Curr. Opin. Pharmacol. (2005) 5(6):612-617.

Rantakokko, J. et al., "Expression profiles of mRNAs for osteoblast and osteoclast proteins as indicators of bone loss in mouse immobilization osteopenia model," J. Bone Min. Res. (1999) 14:1934-1942.

Reidhaar-Olson, J.F. et al., "Active variants of human parathyroid hormone (1-34) with multiple amino acid substitutions," Mol. Cell Endocrinol. (2000) 160:135-147.

Riggs, B.L. et al., "Sex steroids and the construction and conservation of the adult skeleton," Endocr. Rev. (2002) 23:279-302.

Rixon, R.H. et al., "Parathyroid hormone fragments may stimulate bone growth in ovariectomized rats by activating adenylyl cyclase," J. Bone Min. Res. (1994) 9:1179-1189.

Rosol, T.J. et al., "Sequences of the cDNAs encoding canine parathyroid hormone-related protein and parathyroid hormone," Gene (1995) 160(2):241-243.

Ryder, K.D. et al., "Parathyroid hormone modulates the response of osteoblast-like cells to mechanical stimulation," Calcif. Tissue Int. (2000) 67:241-246.

Sakata, T. et al., "Skeletal unloading induces resistance to insulin-like growth factor-I (IGF-I) by inhibiting activation of the IGF-I signaling pathways," J. Bone Min. Res. (2004) 19:436-446.

Schiller, P.C. et al., "Anabolic or catabolic responses of MC3T3-E1 osteoblastic cells to parathyroid hormone depend on time and duration of treatment," J. Bone Miner. Res. (1999) 14(9):1504-1512.

Shackelford, L.C. et al., "Resistance exercise as a countermeasure to disuse-induced bone loss," J. Appl. Physiol. (2004) 97:119-129.

Sheng, M.H. et al., "High osteoblastic activity in C3H/HeJ mice compared to C57BL/6J mice is associated with low apoptosis in C3H/HeJ osteoblasts," Calcif. Tissue Int. (2006) 78:293-301.

Shrader, S.P. et al., "Parathyroid hormone (1-84) and treatment of osteoporosis," Ann. Pharmacother. (2005) 39:1511-1516.

Somjen, D. et al., "Stimulation by defined parathyroid hormone fragments of cell proliferation in skeletal-derived cell cultures," Biochem. J. (1990) 272:781-785.

Takeda, S. et al., "Leptin regulates bone formation via the sympathetic nervous system," Cell (2002) 111:305-317.

Trebacz, H., "Disuse-induced deterioration of bone strength is not stopped after free remobilization in young adult rats," J. Biomech. (2001) 34:1631-1636.

Turner, R.T. et al., "Programmed administration of parathyroid hormone increases bone formation and reduces bone loss in hindlimb-unloaded ovariectomized rats," Endocrinology (1998) 139:4086-4091.

U.S. Department of Health and Human Services, "Bone Health and Osteoporosis: A report of the Surgeon General 2004," Public Health Service, Office of the Surgeon General, Rockville, MD (2004) Executive Summary, 68 pages.

Uusitalo, H. et al., "A metaphyseal defect model of the femur for studies of murine bone healing," Bone (2001) 28:423-429.

Vahle, J.L. et al., "Skeletal changes in rats given daily subcutaneous injections of recombinant human parathyroid hormone (1-34) for 2 years and relevance to human safety," Toxicol. Pathol. (2002) 30:312-321.

Verborgt, O. et al., "Loss of osteocyte integrity in association with microdamage and bone remodeling after fatigue in vivo," J. Bone Min. Res. (2000) 15:60-67.

Vestergaard, P. et al., "Fracture rates and risk factors for fractures in patients with spinal cord injury," Spinal Cord (1998) 36:790-796.

Wang, B.L. et al., "Parathyroid hormone regulates osterix and Runx2 mRNA expression predominantly through protein kinase A signaling in osteoblast-like cells," J. Endocrinol. Invest. (2006) 29:101-108.

Wang, C.M. et al., "Epidemiology of extraspinal fractures associated with acute spinal cord injury," Spinal Cord (2001) 39:589-594.

Watanabe, Y. et al., "Intravenous pamidronate prevents femoral bone loss and renal stone formation during 90-day bed rest," J. Bone Min. Res. (2004) 19:1771-1778.

Weinreb, M. et al., "Osteopenia in the immobilized rat hind limb is associated with increased bone resorption and decreased bone formation," Bone (1989) 10:187-194.

Weinreb, M. et al., "Short-term healing kinetics of cortical and cancellous bone osteopenia induced by unloading during the reloading period in young rats," Virchows Arch. (1997) 431:449-452.

Young, Stacey. "Bear Bones," ScienCentralNews, http://www.sciencentral.com/articles/view.php3?article_id=218392188&language=english (Feb. 27, 2004) 3 pages.

Yuan, Z.Z. et al., "Parathyroid hormone therapy accelerates recovery from immobilization-induced osteopenia," Bone (1995) 17:219S-223S.

Zanchetta, J.R. et al., "Effects of teriparatide [recombinant human parathyroid hormone (1-34)] on cortical bone in postmenopausal women with osteoporosis," J. Bone Min. Res. (2003) 18:539-543.

Zayzafoon, M. et al., "Modeled microgravity inhibits osteogenic differentiation of human mesenchymal stem cells and increases adipogenesis," Endocrinology (2004) 145(5):2421-2432.

Zerwekh, J.E. et al., "The effects of twelve weeks of bed rest on bone histology, biochemical markers of bone turnover, and calcium homeostasis in eleven normal subjects," J. Bone Miner. Res. (1998) 13:1594-1601.

Zhang, C-X. et al., "Identification of carboxyl-terminal peptide fragments of parathyroid hormone in human plasma at low-picomolar levels by mass spectrometry," Anal. Chem. (2006) 78:1636-1643.

Donahue, S.W. et al., "Anabolic activity of black bear PTH," Bone (2008) 42:S69-S70 (abstract only).

European Patent Office Action for Application No. 06846290.2 dated Oct. 21, 2010 (5 pages).

Israeli Patent Office Action for Application No. 191250 dated Aug. 1, 2010 (2 pages).

International Search Report and Written Opinion for Application No. PCT/US2006/060844 dated Jun. 22, 2007 (16 pages).

International Search Report and Written Opinion for Application No. PCT/US2009/066974 dated Oct. 13, 2010 (9 pages).

Chinese Patent Office Action for Application No. 2006800050702.4 dated Mar. 22, 2011 (8 pages).

* cited by examiner

3 Month Hibernation Period

```
                        1           2          3         4
                        0           0          0         0
monkey  SVSEIQLMHNLGKHLNSMERVEWLRKKLQDVHNFIALGAP
human   SVSEIQLMHNLGKHLNSMERVEWLRKKLQDVHNFVALGAP
horse   SVSEIQLMHNLGKHLNSVERVEWLRKKLQDVHNFIALGAP
dog     SVSEIQFMHNLGKHLSSMERVEWLRKKLQDVHNFVALGAP
cat     SVSEIQFMHNLGKHLSSVERVEWLRRKLQDVHNFVALGAP
bear    SVSEIQFMHNLGKHLSSMERVEWLRKKLQDVHNFVALGAP
bovine  AVSEIQFMHNLGKHLSSMERVEWLRKKLQDVHNFVALGAS
pig     SVSEIQLMHNLGKHLSSLERVEWLRKKLQDVHNFVALGAS
rat     AVSEIQLMHNLGKHLASVERMQWLRKKLQDVHNFVSLGVQ
mouse   AVSEIQLMHNLGKHLASMERMQWLRRKLQDMHNFVSLGVQ 4            5          6            7          8  8
         1            0          0            0          0  4
monkey  LAPRDAGSQRPRKKEDNILVESHEKSLGEADKADVDVLTKAKSQ
human   LAPRDAGSQRPRKKEDNVLVESHEKSLGEADKADVDVLTKAKSQ
horse   IFHRDGGSQRPRKKEDNVLIESHQXSLGEADKADVDVLSKTKSQ
dog     IAHRDGSSQRPLKKEDNVLVESYQKSLGEADKADVDVLTKAKSQ
cat     IAHRDGGSQRPRKKEDNVPAENHQKSLGEADKADVDVLIKAKSQ
bear    TAHRDGGSQRPQKKEDNVLVENHQKSLGEADKADVDVLTKSKPQ
bovine  IAYRDGSSQRPRKKEDNVLVESHQKSLGEADKADVDVLIKAKPQ
pig     IVHRDGGSQRPRKKEDNVLVESHQKSLGEADKAAVDVLIKAKPQ
rat     MAAREGSYQRPTKKEENVLVDGNSKSLGEGDKADVDVLVKAKSQ
mouse   MAARDGSHQKPTKKEENVLVDGNPKSLGEGDKADVDVLVKSKSQ
```

FIG. 5

METHODS OF USING BLACK BEAR PARATHYROID HORMONE

CROSS-REFERENCE TO RELATED APPLICATIONS

This application claims the benefit of U.S. Provisional Application No. 60/736,145, filed Nov. 10, 2005, which is incorporated herein by reference in its entirety.

STATEMENT REGARDING FEDERALLY-SPONSORED RESEARCH

This invention was made with United States government support awarded by the National Institutes of Health (NIAMS AR050420 and NIA R21AA 14399-01A2) and the National Science Foundation (IBN-0343515). The United States government has certain rights in this invention.

BACKGROUND

Bone loss diseases are currently a health threat for approximately 44 million Americans, including 10 million with osteoporosis and 34 million with low bone mass and at risk for developing osteoporosis. The number of Americans with osteoporosis is expected to rise by 2020. Consequently, a large number of individuals are at risk for bone fracture due to low bone mass. Approximately 40% of white women and 13% of white men over age 50 are at risk for hip, spine, or forearm fracture within their lifetime. The costs associated with osteoporosis-related fractures were approximately $18 billion dollars in 2002, and are expected to continue climbing. In addition to primary (age-related) osteoporosis, disuse osteoporosis is an important clinical problem, especially for patients chronically immobilized due to stroke or spinal cord injury. Fracture rates double compared to healthy controls in the first year following spinal cord injury and are also elevated compared to healthy controls after the onset of stroke. Disuse increases fracture rates primarily because reduced skeletal loading causes unbalanced bone remodeling which leads to bone loss.

SUMMARY

In one embodiment, the invention provides an isolated polypeptide comprising at least 10 consecutive amino acid residues of SEQ ID NO: 2 wherein the polypeptide comprises at least one of amino acid residues 41 and 52 of SEQ ID NO: 2. The present invention also provides an isolated polynucleotide comprising SEQ ID NO: 1.

In another embodiment, the invention provides a method of increasing cAMP levels in a bone-forming cell comprising contacting the bone-forming cell with an effective amount of a polypeptide comprising amino acid residues 1-34 of SEQ ID NO: 2, wherein contacting the bone-forming cell with the polypeptide increases cAMP levels in the bone-forming cell.

In yet another embodiment, the invention provides a method of reducing apoptosis in a bone-forming cell comprising contacting the bone-forming cell with an effective amount of a polypeptide comprising amino acid residues 1-34 of SEQ ID NO: 2, wherein contacting the bone-forming cell with the polypeptide reduces apoptosis in the bone-forming cell.

In still another embodiment, the invention provides a method of decreasing the ratio of expression levels of Bax protein to Bcl-2 protein in a bone-forming cell comprising contacting the bone-forming cell with an effective amount of a polypeptide comprising amino acid residues 1-34 of SEQ ID NO: 2, wherein contacting the bone-forming cell with the polypeptide decreases the ratio of expression levels of Bax protein to Bcl-2 protein in the bone-forming cell.

In yet another embodiment, the invention provides a method of increasing the expression level of a bone matrix protein, a transcriptional activator, or a transcriptional regulator in a bone-forming cell comprising contacting the bone-forming cell with an effective amount of a polypeptide comprising amino acid residues 1-34 of SEQ ID NO: 2, wherein contacting the bone-forming cell with the polypeptide increases the expression level of the bone matrix protein, the transcriptional activator, or the transcriptional regulator in the bone-forming cell.

In still another embodiment, the invention provides a method of enhancing bone mineral density, increasing bone mass, decreasing bone loss, or reducing the incidence of bone fractures in a subject, comprising contacting a bone-forming cell in the subject with an effective amount of a polypeptide comprising amino acid residues 1-34 of SEQ ID NO: 2, wherein contacting the bone-forming cell with the polypeptide enhances bone mineral density, increases bone mass, decreases bone loss, or reduces the incidence of bone fractures in the subject.

In yet another embodiment, the invention provides a method of enhancing bone mineral density, increasing bone mass, decreasing bone loss, or reducing the incidence of bone fractures, or any combination thereof, in a subject, comprising contacting a bone-forming cell in the subject with an effective amount of a polypeptide comprising bear parathyroid hormone or a functional fragment thereof, wherein contacting the bone-forming cell with the polypeptide enhances bone mineral density, increases bone mass, decreases bone loss, or reduces the incidence of bone fractures in the subject.

In still another embodiment, the invention provides an isolated polypeptide consisting essentially of amino acid residues 1-34 of SEQ ID NO: 2.

In yet another embodiment, the invention provides an isolated polypeptide consisting essentially of amino acid residues 1-36 of SEQ ID NO: 2.

BRIEF DESCRIPTION OF THE DRAWINGS

FIG. 5 shows the sequence of the mature black bear PTH protein (SEQ ID NO: 2) compared to other known PTH sequences, including monkey (SEQ ID NO: 5), human (SEQ ID NO: 6), horse (SEQ ID NO: 7), dog (SEQ ID NO: 8), cat (SEQ ID NO: 9), bovine (SEQ ID NO: 10), pig (SEQ ID NO: 11), rat (SEQ ID NO: 12), and mouse (SEQ ID NO: 13).

DETAILED DESCRIPTION

In humans and most other mammals, factors such as aging and extended periods of disuse can lead to osteoporosis and an increased risk of fracture. Disuse due to spinal cord lesion significantly decreases bone mineral density, particularly in the tibia and femur, and significantly reduces the cross-sectional moment of inertia of the femoral diaphysis. Thus, bone bending strength is reduced by spinal cord injury and fracture risk is increased. Disuse due to stroke also increases fracture risk. In addition, mechanical unloading of bone can cause rapid bone loss due to immediate increases in bone resorption in addition to sustained decreases in bone formation. Disuse-induced changes in bone remodeling increase intracortical porosity, and reduce the cross-sectional and mechanical properties of long bone diaphyses. Unloading also considerably reduces trabecular bone mass and microarchitecture.

The deleterious effects of disuse on bone may continue into the remobilization period. Some bone may be recovered during remobilization, but recovery is slow and often incomplete. For example, the rate of bone loss during bedrest is more than three times greater than the rate of bone gain during remobilization, and the recovery of bone lost in spaceflight can be incomplete even after 5 years. When disuse-induced changes in bone can be completely reversed by resumed activity, the remobilization period is often 2 to 3 times longer than the immobilization period. Bone formation decreases and/or bone resorption increases in many situations that reduce mechanical loads on bone. However, both resorption and formation increase during canine forelimb immobilization, yet there is significant bone loss in that case. Likewise, thigh bone turnover occurs in patients with spinal cord injury, which leads to bone loss and increased fracture incidence.

Figure 1:
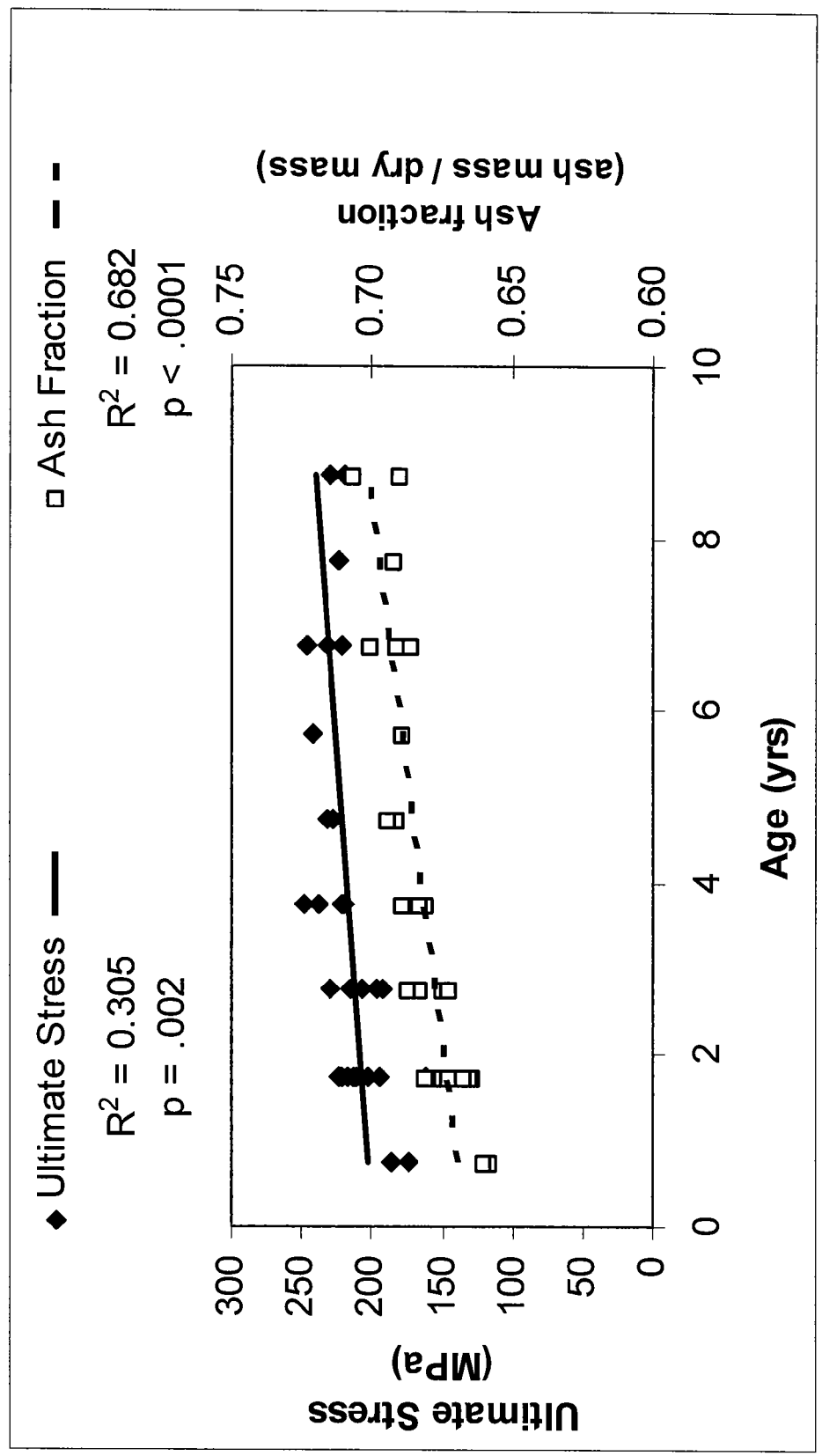
FIG. 1 shows ultimate stress, a measure of bone strength, and ash fraction, a measure of bone mineral content, which both increase with age in black bears.

In contrast to this, black bears do not suffer significant bone loss due either to aging (FIG. 1) or, more importantly, to the extended periods of disuse that occur during hibernation. Hibernating black bears have immobilization and active periods that can be approximately equal in length in northern regions. Data on serum markers of bone metabolism (see below) suggest that both resorption and formation increase during disuse in bears, with a normal lag time (i.e., reversal period) between resorption and formation, and that the increase in formation remains coupled and balanced with the increase in resorption. Histological data from black bear iliac crest biopsies also show increased resorption and formation during inactivity. However, bears are unique in that trabecular bone volume, bone mineral density, and bone mineral content do not decrease during hibernation. Moreover, cortical bone strength and ash fraction increase with age, and porosity does not change with age in black bears, despite annual periods of disuse. Cortical bone porosity is significantly lower in hibernating grizzly bears than in active grizzly bears, and femoral cross-sectional geometry and strength are unaffected by hibernation.

Bears have evolved many unique biological mechanisms to survive long periods of immobilization without food. These mechanisms appear to include the recycling of calcium and other products of bone catabolism, since bears increase bone turnover but do not excrete waste during hibernation. In humans, bedrest-induced disuse osteoporosis is caused primarily by increased resorption without a corresponding increase in formation. This results in hypercalcemia and a negative calcium balance brought about by increased urinary and fecal calcium. Since bears do not urinate or defecate during hibernation, it is likely that most of the calcium released from bone by resorption is recycled back into bone via osteoblastic bone formation. Ionized calcium is found to increase by about 23% during hibernation, possibly because of the lag time between resorption and formation. Paradoxically, black bear PTH levels are highest when levels of ionized calcium are highest (Table 1). Taken together, these findings suggest that bears have evolved biological mechanisms to avoid osteoporosis.

The mechanisms that uncouple bone formation from resorption during disuse in most animals are unknown, but likely involve both mechanical and biochemical factors. Lack of mechanical strain may lead to increased resorption by initiating osteocyte apoptosis and concomitantly reducing osteoblastic activity. Hormones such as human PTH can sensitize bone cells to mechanical stimulation and synergistically, with mechanical loading, increase bone formation. Human PTH given once daily to humans increases bone mass and decreases fracture incidence. Thus, in black bears, circulating PTH may sensitize bone cells to low levels of mechanical stimulation (possibly due to shivering or repositioning in the hibernaculum) to help maintain bone formation during disuse. PTH may also help maintain bone formation in black bears by stimulating osteoblast differentiation and inhibiting osteoblast apoptosis.

Figure 2:
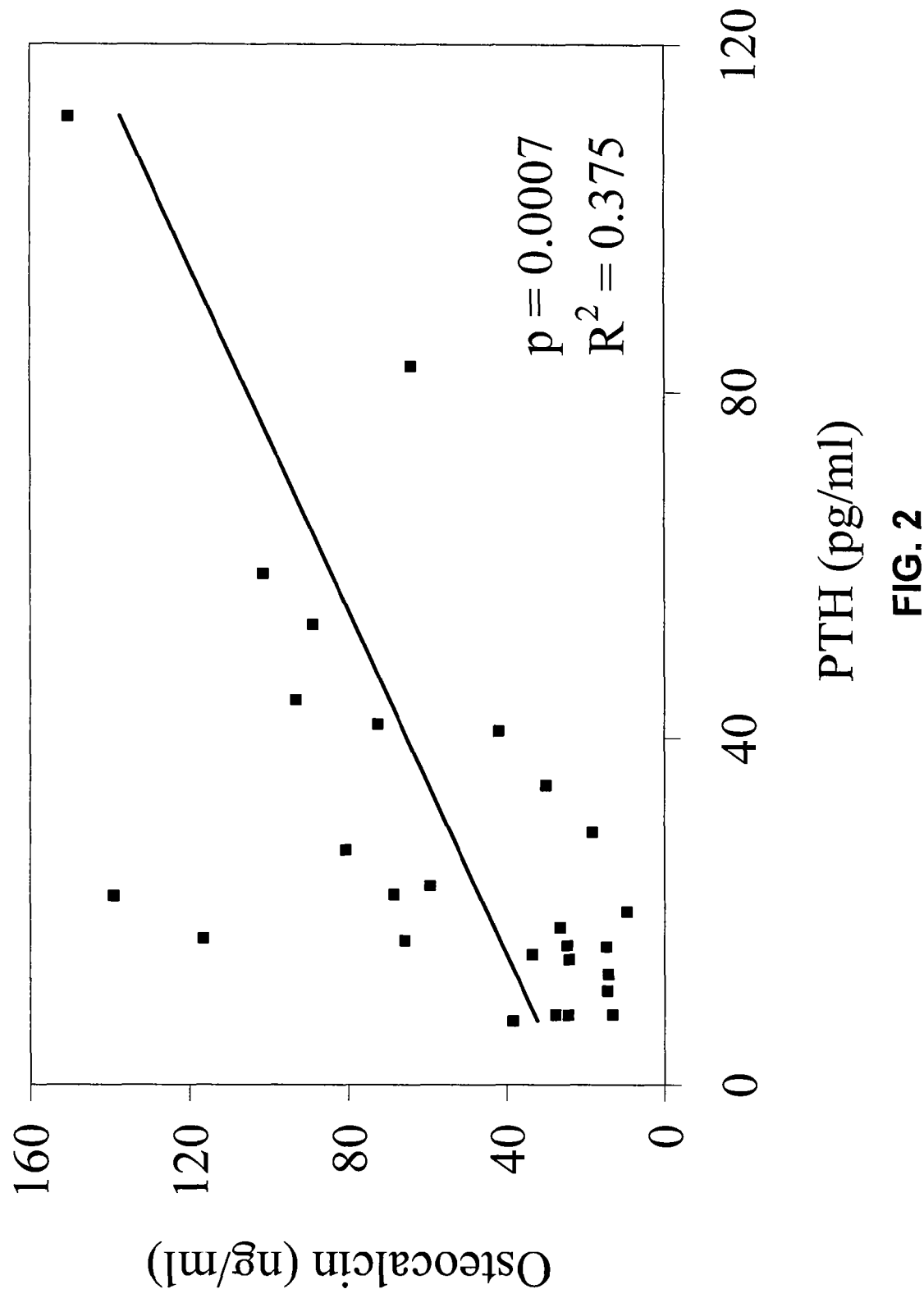
FIG. 2 shows that serum osteocalcin levels are positively correlated with serum parathyroid hormone (PTH) levels (p=0.0007, n=27) in black bears for pooled pre-hibernation, hibernation, and post-hibernation samples.

PTH is the primary regulator of blood calcium levels, and thus plays a role in maintaining homeostatic serum calcium levels in black bears during disuse. Serum PTH levels are positively correlated with the bone formation marker osteocalcin in active and hibernating black bears (FIG. 2), and both osteocalcin and PTH increase during hibernation. In addition, black bear PTH concentration is highest when ionized calcium concentration is highest. Since bone resorption increases during hibernation but total serum calcium (tCa) remains unchanged, increased levels of PTH likely cause increased renal reabsorption of calcium, facilitating the recycling of mineral back into the bone with a balanced increase in bone formation. This leads to the observed preservation of trabecular and cortical bone properties like bone mineral density ("BMD") and cortical porosity. Bone resorption increases during hibernation, but blood calcium concentration remains constant despite the fact that bears do not excrete waste during hibernation. The calcium liberated by bone resorption during hibernation may be recycled and put back into bone by maintaining balanced coupling of bone formation with bone resorption. This supports the idea that PTH has anabolic effects in hibernating black bears and provides an explanation for the bears' distinctive ability to maintain balanced bone remodeling during hibernation. The anabolic effects of PTH may be enhanced in black bears when physical activity is resumed following arousal from hibernation. Mechanical loading and human PTH have previously been shown to act synergistically to increase bone formation in vivo in rats and biochemical signaling in vitro. During remobilization in the spring, bone formation in the black bear, as indicated by serum osteocalcin, remains higher than pre-hibernation levels.

The sequence for the polynucleotide which encodes black bear (*Ursus americanus*) parathyroid hormone (PTH) (SEQ ID NO: 1) was discovered as well as the polypeptide sequence for the mature 84 amino acid PTH protein (SEQ ID NO: 2). In addition, the cDNA (SEQ ID NO: 3) which encodes the full length PTH protein (SEQ ID NO: 4), including a 25 amino acid signal peptide (amino acid residues 1-25 of SEQ ID NO: 4) and a 6 amino acid propeptide (amino acid residues 26-31 of SEQ ID NO: 4) has been sequenced. The mature black bear PTH protein differs from other known PTH proteins (FIG. 5).

Compared to human PTH, black bear PTH has 11 different amino acid residues out of a total of the 84 amino acid residues of the full-length, mature PTH polypeptide. Also described herein are various methods of use for black bear PTH and functional fragments thereof. It is specifically envisioned that polypeptide subfragments comprising at least 10 consecutive amino acid residues of SEQ ID NO: 2 and including at least one of amino acid residues 41 or 52 can be used to develop antibodies specific for black bear PTH. These antibodies can be used to quantify black bear PTH, e.g. in an ELISA assay.

PTH receptors on the surface of bone-forming cells are coupled to cyclic adenosine monophosphate (cAMP)-dependent second-messenger signaling pathways inside the cells. These signaling pathways, in turn, lead to increased expression of genes involved in bone formation such as those encoding type I collagen, osteonectin, and osteopontin. Since the cAMP/protein kinase A pathway is responsible for the majority of PTH-induced increases in histological and serum indices of bone formation, it follows that an increased cAMP response can lead to greater bone formation. A relatively small number of amino acid substitutions in the sequence of a given PTH protein can stimulate greater cyclic adenosine monophosphate (cAMP) production compared to the native form. For example, ovariectomized rats demonstrated a 25% greater bone formation response to daily 25 μg injections of bovine PTH 1-34 than to rat PTH 1-34, where rat PTH 1-34 has 5 amino acid sequence differences compared to bovine PTH 1-34. Injection of bovine PTH 1-34 results in a 37% greater increase in bone volume fraction during treatment.

Thus, it is likely that the amino acid substitutions in black bear PTH cause it to induce greater cAMP production in bone-forming cells than human PTH. PTH, in general, elicits a greater bone formation response by mechanisms such as decreasing osteoblast apoptosis, increasing osteoblast differentiation via Runx2, downregulating SOST-based negative feedback in osteocytes, and increasing production of mRNA for bone matrix proteins, all via cAMP-mediated pathways. Although it is not necessary to understand the mechanism of an invention, it is believed that black bear PTH is likely more osteogenic than other forms of PTH, which explains why black bears are uniquely able to maintain balanced bone remodeling during disuse. In another embodiment of the present invention, contacting a bone-forming cell with black bear PTH or a functional fragment thereof increases cAMP levels in the bone-forming cell. In another embodiment of the present invention, the bone-forming cell is contacted with a polypeptide comprising amino acid residues 1-34 or 1-36 of SEQ ID NO: 2. In another embodiment of the present invention, the bone-forming cell is contacted with a polypeptide comprising SEQ ID NO: 2. In another embodiment, the bone-forming cell is contacted with a polypeptide comprising amino acid residues 11-84 or 7-84 of SEQ ID NO: 2.

As used herein, "contacting a cell" with a PTH polypeptide includes adding the polypeptide to the culture solution, in the case of in vitro experiments, or administering the polypeptide to a subject using appropriate administration procedures for polypeptide therapeutic agents. "Contacting a cell" also includes introducing into a subject an exogenous polynucleotide that encodes the desired polypeptide in an expression system so as to synthesize and release the polypeptide in the subject. As used herein, "bone-forming cells" includes, but is not limited to, osteoblasts, osteocytes, bone lining cells, chondroblasts, and chondrocytes. Suitably, the bone-forming cell may be in a subject.

Bone-forming cells regularly turn over, with most of the cells' death being due to programmed cell death, or apoptosis. Given this regular rate of turnover, any mechanism that decreases apoptosis of bone-forming cells will lead to an increased number of bone-forming cells which presumably will promote bone growth. Thus, in another embodiment of the present invention, contacting a bone-forming cell with black bear PTH or a functional fragment thereof reduces apoptosis in the bone-forming cell. In another embodiment of the present invention, the bone-forming cell is contacted with a polypeptide comprising amino acid residues 1-34 or 1-36 of SEQ ID NO: 2. In another embodiment of the present invention, the bone-forming cell is contacted with a polypeptide comprising SEQ ID NO: 2.

Moreover, it is possible that several of the larger C-terminal fragments of endogenous black bear PTH play a role in seasonal bone remodeling processes via binding to CPTHRs (C-terminal PTH receptors). Specifically, C-terminal fragments of bear PTH may antagonize the calcemic effects of PTH 1-84 and 1-34 by preventing osteoclastogenesis and possibly by affecting mature osteoclast activity that would normally occur in response to resorptive stimuli such as disuse (Divieti, P. et al., 2002, Endocrinology 143(1): 171-6). This may help bears to maintain homeostatic calcium levels throughout hibernation. Thus, in another embodiment of the present invention, osteocytes and osteoblasts may be contacted with a polypeptide comprising amino acid residues 11-84 or 7-84 of SEQ ID NO: 2.

The protein Bax promotes apoptosis while the Bcl-2 protein protects cells from apoptosis, and a decrease in the expression ratio of Bax to Bcl-2 is indicative of a decrease in apoptosis in the particular cell population. Thus, in another embodiment of the present invention, contacting a bone-forming cell with black bear PTH or a functional fragment thereof decreases the ratio of expression levels of Bax protein relative to expression levels of Bcl-2 protein in the bone-forming cell. In another embodiment of the present invention, the bone-forming cell is contacted with a polypeptide comprising amino acid residues 1-34 or 1-36 of SEQ ID NO: 2. In another embodiment of the present invention, the bone-forming cell is contacted with a polypeptide comprising SEQ ID NO: 2. In another embodiment of the present invention, the bone-forming cell is contacted with a polypeptide comprising amino acid residues 11-84 or 7-84 of SEQ ID NO: 2.

Figure 7:
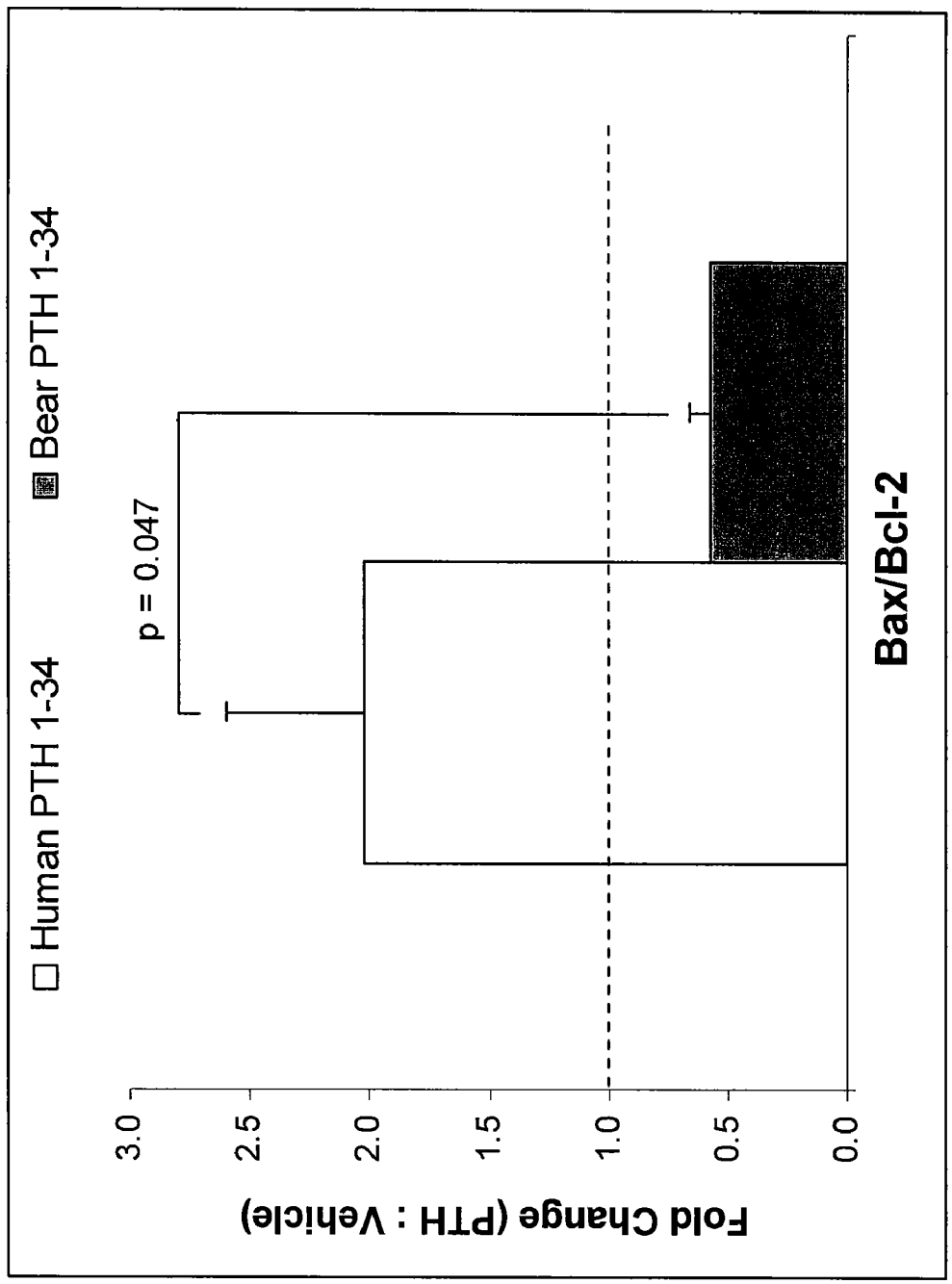
FIG. 7 shows the effects of human and black bear PTH 1-34 on apoptosis-related gene expression (n=4).

Example 11 shows that black bear PTH 1-34 decreases the expression ratio of Bax/Bcl-2 in cultured cells whereas human PTH 1-34 increases the expression ratio of Bax/Bcl-2 (FIG. 7). Thus, black bear PTH 1-34 appears to be more effective at preventing apoptosis than human PTH 1-34. Without being bound by theory, this difference may be the result of the two amino acid differences between human and black bear PTH 1-34. These data suggest that bear PTH is more anabolic than human PTH, since decreased osteoblast apoptosis may contribute to the bone formation response induced by PTH treatment.

Contacting a bone-forming cell with black bear PTH or a functional fragment thereof also increases the expression level of bone matrix protein, a transcriptional activator, or a transcriptional regulator in the bone-forming cell. In another embodiment of the present invention, the transcriptional activator is Runx2. In another embodiment of the present invention, the transcriptional regulator is c-fos. Bone matrix proteins may suitably include osteocalcin, osteopontin, and type I collagen. In another embodiment of the present invention, the bone-forming cell is contacted with a polypeptide comprising amino acid residues 1-34 or 1-36 of SEQ ID NO: 2. In another embodiment of the present invention, the bone-forming cell is contacted with a polypeptide comprising SEQ ID NO: 2. In another embodiment of the present invention, the bone-forming cell is contacted with a polypeptide comprising amino acid residues 11-84 or 7-84 of SEQ ID NO: 2.

Exogenous human PTH is used to treat post-menopausal and age-related osteoporosis in humans, but it is not an ideal therapeutic. Only recombinant human PTH 1-34 (LY333334, Eli Lilly, Indianapolis Ind.) is currently approved for clinical use, and only one form of recombinant human PTH 1-84 is under consideration for approval by the U.S. Food and Drug Administration (ALX1-11, NPS Pharmaceuticals, Parsippany, N.J.). Though LY333334 and ALX1-11 can stimulate approximately the same magnitude of bone formation in vivo, their biological actions are not identical. For example, PTH 1-34 down-regulates production of procollagen-1 mRNA, whereas PTH 1-84 does not (Nasu et al., 1998, *Endocr J*, 45, 229-34). In addition, it has also been determined that the C-terminal portion of human PTH, when cleaved from the mature hormone, has important biological functions such as inhibition of bone resorption.

Long-term usage of either LY333334 or ALX1-11 generates osteosarcoma in rats, but preliminary results indicate that human PTH 1-84 has a lower rate of carcinogenicity than human PTH 1-34, possibly because C-terminal fragments of exogenous human PTH 1-84 (arising from peripheral proteolytic processing) can bind to C-terminal PTH receptors (CPTHRs) and increase osteocyte apoptosis. Thus, though equally anabolic, human PTH 1-84 may be a superior osteoporosis therapy compared to human PTH 1-34. However, human PTH 1-84 cannot completely restore lost bone; it has been suggested that men and women can lose between 20-30% of cortical and cancellous bone due to age-related osteoporosis, but only 8% is recovered using ALX1-11 during its suggested treatment regimen. Therefore, there exists a clinical need for osteoporosis treatments with greater osteogenic capabilities.

In an additional embodiment of the present invention, contacting a bone-forming cell in a subject with black bear PTH or a functional fragment thereof increases bone mineral density, increases bone mass, decreases bone loss or reduces the incidence of bone fracture in the subject. In another embodiment of the present invention, the bone-forming cell is contacted with a polypeptide comprising amino acid residues 1-34 or 1-36 of SEQ ID NO: 2. In another embodiment of the present invention, the bone-forming cell is contacted with a polypeptide comprising SEQ ID NO: 2. In another embodiment of the present invention, the bone-forming cell is contacted with a polypeptide comprising amino acid residues 11-84 or 7-84 of SEQ ID NO: 2.

Suitably, contacting a bone-forming cell in a subject with black bear PTH or a functional fragment thereof increases bone mineral density, increases bone mass, decreases bone loss or reduces the incidence of bone fracture by at least about 5% or at least about 10%. The increase in bone mineral density, increase in bone mass, decrease in bone loss or reduction in the incidence of bone fracture may be at least about 15%, at least about 30%, at least about 50%, at least about 75% or at least about 90%. The increase in bone mineral density, increase in bone mass, decrease in bone loss or reduction in the incidence of bone fracture is determined by measuring the desired characteristic on the same patient before and after treatment by a technique known to one of ordinary skill in the art. For example, bone mineral density can be determined by methods involving taking dual energy x-rays (DEXA) or CT scans of bones in the spinal column, wrist, arm or leg.

The subject may suitably be a mammal, including without limitation human, horse, dog, cat, mouse, bear, bovine, pig, or deer. The subject may have osteoporosis or may be at risk to develop osteoporosis. Risk factors for developing osteoporosis include: personal history of fracture after age 50; current low bone mass; history of fracture in a first-degree relative; being female; being thin and/or having a small frame; advanced age; a family history of osteoporosis; estrogen deficiency as a result of menopause, especially early or surgically induced; abnormal absence of menstrual periods (amenorrhea); anorexia nervosa; low lifetime calcium intake; vitamin D deficiency; use of certain medications (corticosteroids, chemotherapy, anticonvulsants and others); presence of certain chronic medical conditions, such as those that decrease calcium absorption in the gut such as Crohn's disease; low testosterone levels in men; an inactive lifestyle; current cigarette smoking; excessive use of alcohol; and being Caucasian or Asian; although African Americans and Hispanic Americans are at significant risk as well. Moreover, women can lose up to 20 percent of their bone mass in the five to seven years following menopause, making them more susceptible to osteoporosis.

Black bear PTH or functional fragments thereof are also useful as a preventative (rather than a restorative), or prophylactic, measure to combat disuse osteoporosis or to prevent osteoporosis in a subject at risk for developing osteoporosis. Since bears appear to be the only animals that maintain balanced bone remodeling during disuse, black bear PTH or functional fragments thereof are also useful to prevent bone loss during reduced skeletal unloading that occurs, for example, in astronauts during spaceflight and in spinal cord injury patients after injury.

Black bear PTH or functional fragments thereof may be administered in combination with calcium and/or vitamin D. The calcium and/or vitamin D may be administered concurrently with black bear PTH or functional fragment thereof or may be administered before or after black bear PTH or functional fragments thereof. Suitably, "Vitamin D" refers to the entire Vitamin D class of compounds.

Administration of black bear PTH or functional fragments thereof or compositions comprising black bear PTH or functional fragments thereof can be accomplished by any suitable technique. Black bear PTH or functional fragment thereof may be administered by any suitable route including, for example, oral, nasal, rectal, and parenteral routes of administration. As used herein, the term parenteral includes but is not limited to subcutaneous, intradermal, intravenous, intramuscular, intraperitoneal, and intrathecal administration, such as by injection. As is discussed above, administration of a polypeptide includes administration of an exogenous polynucleotide operably connected to a promoter such that the polynucleotide expresses the polypeptide in the subject. Administration of the polypeptide also includes administration of a viral vector comprising a polynucleotide encoding the polypeptide. Suitably, the viral vector is an adenoviral vector.

Black bear PTH or functional fragments thereof, or compositions comprising black bear PTH or functional fragments thereof, can be administered continuously or at discrete time intervals as can be readily determined by a person skilled in the art. An ordinarily skilled clinician can determine a suitable amount of black bear PTH or a functional fragment thereof to be administered to a subject.

The specific effective dose for any particular subject will depend upon a variety of factors, including the disorder being treated and the severity of the disorder; activity of the specific compound employed; the specific composition employed; the age, body weight, general health, sex and diet of the subject; route of administration; the rate of excretion or inactivation of black bear PTH or functional fragments thereof employed;

the duration of the treatment; other pharmaceuticals used in combination or coincidental with black bear PTH or functional fragments thereof and like factors well known in the medical arts. For example, it is well within the level of ordinary skill in the art to start doses at levels lower than those required to achieve the desired effect and to gradually increase the dosage until the desired effect is achieved.

Suitably, the dosage of black bear PTH or functional fragments thereof in one embodiment is in a range of 0.10 µg/kg per day to 40 µg/kg per day. In another embodiment, the dosage is in a range of 5 µg/kg per day to 20 µg/kg per day. In still another embodiment, the dosage is 10 µg/kg per day. In another embodiment, the dosage is in a range of 10 µg/day to 400 µg/day per subject. In yet another embodiment, the dosage is in a range of 20 µg/day to 40 µg/day per subject. In still another embodiment, the dosage is 30 µg/day per subject. In one embodiment the subject is a human. Suitably, the daily dosages in one embodiment are given for one week, in another embodiment for one month, in yet another embodiment for three months, in yet another embodiment for six months, in still another embodiment for one year, in yet another embodiment for one and a half years, in still another embodiment for two years, and in yet another embodiment for three years.

If desired, the effective daily dose may be divided into multiple doses for purposes of administration. Consequently, single dose compositions may contain such amounts or submultiples thereof to make up the daily dose. If desired, a suitable delivery device is loaded with the effective daily dose for more than one day, for example, for seven days, fourteen days, twenty-one days, twenty-eight days or the like, and the delivery device is used to repeatedly administer the desired daily single dose or daily multiple doses for the desired total number of days. As noted, those of ordinary skill in the art will readily optimize effective doses and co-administration regimens as determined by good medical practice and the clinical condition of the individual subject.

Compositions containing black bear PTH or functional fragments thereof useful in the methods of the present invention can be formulated according to known methods for preparing pharmaceutically useful compositions. Formulations are described in detail in a number of sources which are well known and readily available to those skilled in the art. For example, Remington's Pharmaceutical Science, by E. W. Martin, describes formulations which can be used in the disclosed methods. In general, the compositions will be formulated such that an effective amount of the polypeptide is combined with a suitable carrier in order to facilitate effective administration of the composition.

The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The form will depend on the intended mode of administration and therapeutic application. The compositions also suitably include conventional pharmaceutically acceptable excipients which are known to those skilled in the art. Examples of excipients include water for injection, ethanol, dimethyl sulfoxide, glycerol, alumina, starch, glacial acetic acid, sodium acetate, mannitol, metacresol, hydrochloric acid and/or sodium hydroxide to adjust the pH of a composition to a suitable value, and equivalent or otherwise suitable carriers and diluents. To provide for the administration of such dosages for the desired application, pharmaceutical compositions will comprise between about 0.1% and 99%, and suitably between about 1 and 15% by weight of the total of one or more of the polypeptides of the present invention based on the weight of the total composition including the carrier or diluent.

As used herein, an "isolated" nucleic acid molecule, polynucleotide, polypeptide, or the like, as the case may be, refers to a component that is at least partially purified from contaminants (e.g., other species of polynucleotides, polypeptides, or the like) that is found other than in its natural state. An isolated nucleic acid, polynucleotide, or polypeptide may contain less than about 50%, suitably less than about 75%, and most suitably less than about 90%, of the cellular components with which it was originally associated. A polynucleotide amplified using PCR so that it is sufficiently and easily distinguishable (on a gel, for example) from the rest of the cellular components is considered "isolated". The nucleic acid molecules, polynucleotides, and polypeptides of the invention may be "substantially pure," i.e., having the highest degree of purity that can be achieved using purification techniques known in the art.

As used herein, a "functional fragment" refers to any region or portion of a polypeptide or polynucleotide which is a region or portion of a larger polypeptide or polynucleotide, the region or portion having an activity or function attributable to the larger polypeptide or polynucleotide. For example, a functional fragment of human PTH is the 1-34 region of human PTH.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. All publications, patents and patent applications are herein expressly incorporated by reference in their entirety for all purposes to the same extent as if each individual publication or patent application was specifically and individually incorporated by reference. In case of conflict between the present disclosure and the incorporated patents, publications and references, the present disclosure should control.

It also is specifically understood that any numerical range recited herein includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. If a concentration range is "at least 5%," it is intended that all percentage values up to and including 100% are also expressly enumerated. These are only examples of what is specifically intended.

The following Examples are provided to assist in a further understanding of the invention. The particular materials, methods and conditions employed are intended to be illustrative of the invention and are not limiting upon the scope of the invention.

Example 1

Sequencing of Black Bear PTH 1-84

Genomic DNA Extraction

Blood was collected from a captive female black bear and stored at 4° C. Genomic DNA was extracted from the whole blood samples within 2 weeks, using the GenomicPrep Blood DNA Isolation Kit (Amersham Biosciences, Piscataway, N.J.) according to the manufacturer's instructions.

PCR Cloning and Sequencing

Black bear genomic DNA was used for PCR amplification of PTH, using consensus primers designed based on alignment of eight full-length mammalian PTH sequences available in GenBank including bovine (*Bos taurus*, AAA30749), cat (*Felis catus*, Q9GL67), dog (*Canis familiaris*, P52212), human (*Homo sapiens*, NP_000306), macaque (*Macaca fascicularis*, Q9XT35), mouse (*Mus musculus*, NP_065648), pig (*Sus scrofa*, NP_999566), and rat (*Rattus norvegicus*, NP_058740). PCR amplification was performed using 10-15 ng genomic DNA, 100 µM dNTPs, 0.2 µM each primer, and 1 unit REDTaq (Sigma, St. Louis, Mo.) in 20 µL reaction volume. PCR products were gel-purified using the UltraClean GelSpin Kit (MoBio Carlsbad, Calif.) and cloned into the pCRII vector using the TA cloning kit (Invitrogen, Carlsbad, Calif.). DNA sequencing was performed using the DTCS Quick Start kit and the CEQ8000 Genetic Analysis System (Beckman Coulter, Fullerton, Calif.), following the manufacturer's instructions.

Sequence Analysis

Nucleotide sequences were searched against the GenBank protein database using BlastX (Altschul et al., 1997; Nucleic Acids Res., 25, 3389-402) to confirm their putative identity as PTH. Multiple sequence alignment was performed by ClustalW version 1.82 (Chenna et al., 2003; Nucleic Acids Res., 31, 3497-500). Phylogenetic analysis was carried out using the neighbor-joining (NJ) method implemented in the Molecular Evolutionary Genetics Analysis (MEGA) package version 3.0 (Kumar et al., 2004; Brief Bioinform., 5, 150-63), with the pairwise deletion option for handling alignment gaps, and with the Poisson correction model for distance computation.

PTH Cloning and Sequence Analysis

Various primer combinations were used for PCR-based cloning of PTH from black bear genomic DNA. Based on the sequencing results of preliminary clones, a gene-specific sense primer corresponding to the start codon was designed and used along with a degenerate antisense primer containing the stop codon to amplify the entire coding region of PTH. A second antisense primer covering the stop codon was designed to generate a clone for sequence confirmation.

Sequence assembly revealed a precursor PTH protein of 115 amino acids, including a 25 amino acid signal peptide and a 6 amino acid propeptide. The deduced mature protein is 84 amino acids, with a calculated molecular weight of 9,471 Daltons and a pI of 8.1. Black bear PTH shares 84-95% sequence similarity with other mammalian PTHs, and is most similar to dog PTH (91% identity, 95% similarity) (FIG. 5). Interestingly, two amino acid residues, 41 and 52 of the mature hormone, are unique to black bear PTH.

Example 2

Levels of Bone Resorption and Formation Markers During Hibernation

Serum Samples

Blood samples were collected from five black bears (*Ursus americanus*) held in a captive bear research facility. The Virginia Polytechnic Institute and State University Animal Care Committee approved all bear handling protocols (#98-069-F&WS). The bears were anesthetized with a 2:1 mixture of ketamine (100 mg/ml):xylazine (100 mg/ml); the dosage was 1 cc of the mixture per 45.5 kg of body weight. Body temperatures were 4' to 6° C. cooler during winter collection, confirming that the bears were in a state of hibernation. No urine or scat was present in the hibernation dens. Stressful behavior was not observed during any of the handling procedures. Blood samples were drawn from the femoral vein while the bears were anesthetized, and the samples were transported to the laboratory in an ice-packed cooler. Immediately on return to the laboratory, the blood was centrifuged to isolate the serum, which was frozen at −20° F. Blood samples were collected from each bear every 10 days from the first of October through the end of May. Hibernation began in early January and ended in early April. Thus, the collection dates encompassed an active pre-hibernation period, a disuse hibernation period, and an active post-hibernation remobilization period.

Black Bear Osteocalcin Purification and RIA Procedures

Black bear cortical bone was broken into small fragments, defatted with a mixture of 3 parts hexane and 2 parts isopropanol, and lyophilized. The dried bone was ground to a fine powder under liquid nitrogen, and the osteocalcin was solubilized as described by Hauschka et al. (1989, Physiol. Rev., 69, 990-1047). Osteocalcin was purified from the resulting EDTA extract by a modification of the method of Colombo et al. (1993, J. Bone Miner. Res., 8, 733-43). Briefly, the crude EDTA solution was diluted 2-fold and passed over a bulk column containing 10 g Sepralyte C18 particles (Analytichem International, Harbor City, Calif.) previously activated with methanol and equilibrated with 0.1% trifluoroacetic acid in water (0.1% TFA). An extensive wash with 0.1% TFA was followed by 30% methanol/0.1% TFA until UV absorbance dropped to baseline. Osteocalcin was eluted with 80% methanol/0.1% TFA. Methanol was evaporated under a stream of air and the remaining solution lyophilized. The resulting dried protein was suspended in 0.05 M Tris buffer, pH 8.0 and applied to a 5 ml Biorad Econo-Q column previously equilibrated with the same buffer. The column was developed with a gradient from 0.1 to 0.6 M NaCl in 0.5 M Tris, pH 8.0. Osteocalcin eluted in a symmetric peak, the last to elute from the column. Identity of this peak as osteocalcin was qualitatively verified by reacting fraction aliquots with diazobenzene sulfonic acid yielding a pink color in those fractions containing osteocalcin, with intensity corresponding to peak height. Both the C18 and the Econo-Q column were new and never exposed to protein from other species. Previous experience with other species suggests the final osteocalcin peak is greater than 99% pure. Concentration of black bear osteocalcin in the final elute was determined with BCA reagents from Pierce Chemical (Rockford, Ill.).

Biochemical Assays

The serum was assayed for PTH, 25-OH D, leptin, IGF-I, and osteocalcin (a bone formation marker) using RIA and ELISA.

Highly purified black bear osteocalcin and black bear serum were assayed by radioimmunoassay. The antibody was guinea-pig anti-rat osteocalcin and tracer was $^{125}$I-labeled rat osteocalcin. Dose dilutions of both rat osteocalcin standard (Biomedical Technologies, Inc, Stoughton, Mass.) and purified black bear osteocalcin were included in the assay. Aliquots of 10 µl black bear serum per assay tube were assayed in duplicate, and all samples were assayed at the same time. Duplicates varied by less than 5%.

To observe changes in bone formation and resorption markers during disuse, the mean values of osteocalcin for the 5 black bears were calculated for each time point during the hibernation period. These values were normalized by the maximum osteocalcin value during the hibernation period. Similar calculations were done for measurements of PICP (bone formation marker) and ICTP (bone resorption marker). The normalized values of the resorption and formation markers were plotted on the same graph to assess the temporal and relative magnitude changes in bone resorption and formation during disuse.

Using serum samples from hibernating bears obtained as described above, ionized calcium concentration was measured with an ion-selective electrode (Bayer Rapidlab 865, Leverkusen, Germany).

Using serum samples obtained as described above, PTH was assayed with an ELISA kit from Immutopics International (San Clemente, Calif.); the intra-assay coefficient of variation was 4.7%. 25-OH D was assayed with an ELISA kit from ALPCO Diagnostics (Windham, N.H.); the intra-assay coefficient of variation was 5%. Leptin was measured by RIA (Linco, St. Charles, Mo.); the intra-assay coefficient of variation was 3.4%. IGF-I was measured by acid ethanol extraction RIA (Nichols Institute Diagnostics, San Juan Capistrano, Calif.); the intra-assay coefficient of variation was 4.3%. Serum osteocalcin was measured by RIA as described above. For all the serum metabolites, the mean values (for all bears and all time points within a given season) were calculated for each season (pre-hibernation, hibernation, and post hibernation) and compared by ANOVA. ANOVAs were followed up with Fisher's PLSD tests for multiple mean comparisons. Natural log transformations were used to correct non-constancy of variance for osteocalcin, PTH, 25-OH D, and IGF-I to validate the ANOVAs. Linear regressions were used to assess the correlations between osteocalcin and the hormones. The volume of some serum samples was insufficient to run all assays; sample sizes for each assay are indicated with the results.

Results

Figure 3:
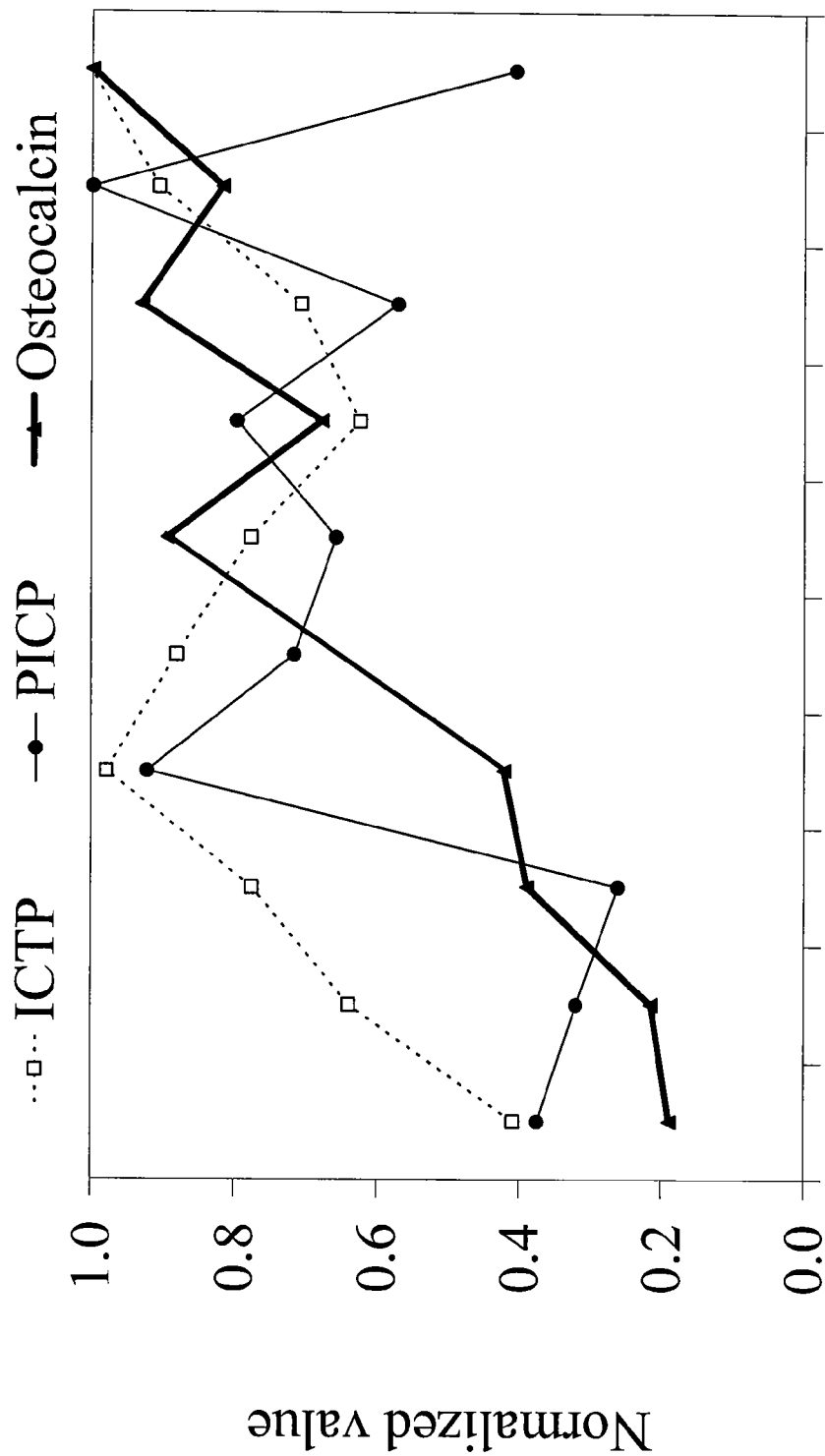
FIG. 3 shows normalized serum resorption (ICTP) and formation (PICP and osteocalcin) marker concentrations during the 3 month disuse period.

The bone resorption marker (ICTP) began to increase immediately after the onset of hibernation (FIG. 3). Each data point is the mean value from 5 bears. After 10-20 days, the bone formation markers (osteocalcin and PICP) also increased and appeared to remain coupled to the increased resorption for the duration of hibernation. This is consistent with the 1-2 week histological "reversal" period between resorption and formation. These remodeling markers showed trends of increased resorption and formation throughout the hibernation period, and formation appeared to remain coupled and balanced with resorption. Mean osteocalcin levels were higher (p<0.0001) during and after hibernation compared to pre-hibernation (Table 1).

Hibernation ionized calcium levels were significantly (p=0.0062) higher than the pre-hibernation levels (Table 1). During remobilization following arousal from hibernation, ionized calcium levels did not significantly (p=0.37) increase relative to hibernation levels, but they remained higher (p=0.015) than pre-hibernation levels.

Osteocalcin was positively correlated with PTH (FIG. 2), but not with 25-OH D, leptin, or IGF-I. PTH was significantly higher in the post-hibernation season than in the pre-hibernation (p=0.006) and hibernation (p=0.014) seasons. The increase in PTH during hibernation relative to pre-hibernation was not significant (p=0.35). 25-OH vitamin D did not show seasonal variations (p=0.64).

Serum leptin did not change during hibernation relative to pre-hibernation, but was significantly (p<0.004) lower during post-hibernation remobilization (Table 1). IGF-1 significantly (p<0.0001) decreased during hibernation relative to pre-hibernation and reached its highest value during remobilization (Table 1).

Example 3

$PGE_2$ Release by MC-3T3 Osteoblasts is Affected by Seasonal Variations in Bear Serum To assess the effects of seasonal variations in bear serum on osteoblast metabolism, MC-3T3 cells were treated with bear serum and prostaglandin $E_2$ ($PGE_2$) release was quantified. MC-3T3 cells were grown in alpha minimum essential media (Invitrogen, Carlsbad, Calif.) supplemented with 10% fetal bovine serum (Hyclone, Logan, Utah) and 1% penicillin-streptomycin solution at 37° C. in 5% $CO_2$ for 24 hours. The media was aspirated and replaced with 10 ml of fresh media containing 10% bear serum collected prior to hibernation, during hibernation, or after hibernation. The cells were allowed to grow for an additional 24 hours, and then the media was collected and frozen at −20° C. for $PGE_2$ analysis. The cells were removed from the culture dishes using 0.25% trypsin in EDTA, pelleted by centrifugation, and quantified with a trypan blue and hemocytometer.

The $PGE_2$ levels were determined using the Biotrak™ $PGE_2$ competitive enzyme immunoassay (Amersham Biosciences, Piscataway, N.J.). The assay was performed in duplicate using 50 µl samples from all experimental media samples. The reaction was halted prior to endpoint determination using 1M sulfuric acid and read at 450 nm using a microplate reader (VERSAmax, Molecular Devices Corporation, Sunnyvale, Calif.). The duplicate optical density values were corrected for nonspecific binding and were averaged, and compared to a standard curve to determine the amount of $PGE_2$ in each well. These values were corrected for total media volume and normalized by the number of cells in the sample. ANOVA was used to compare the normalized $PGE_2$ between the three serum groups.

Figure 4:
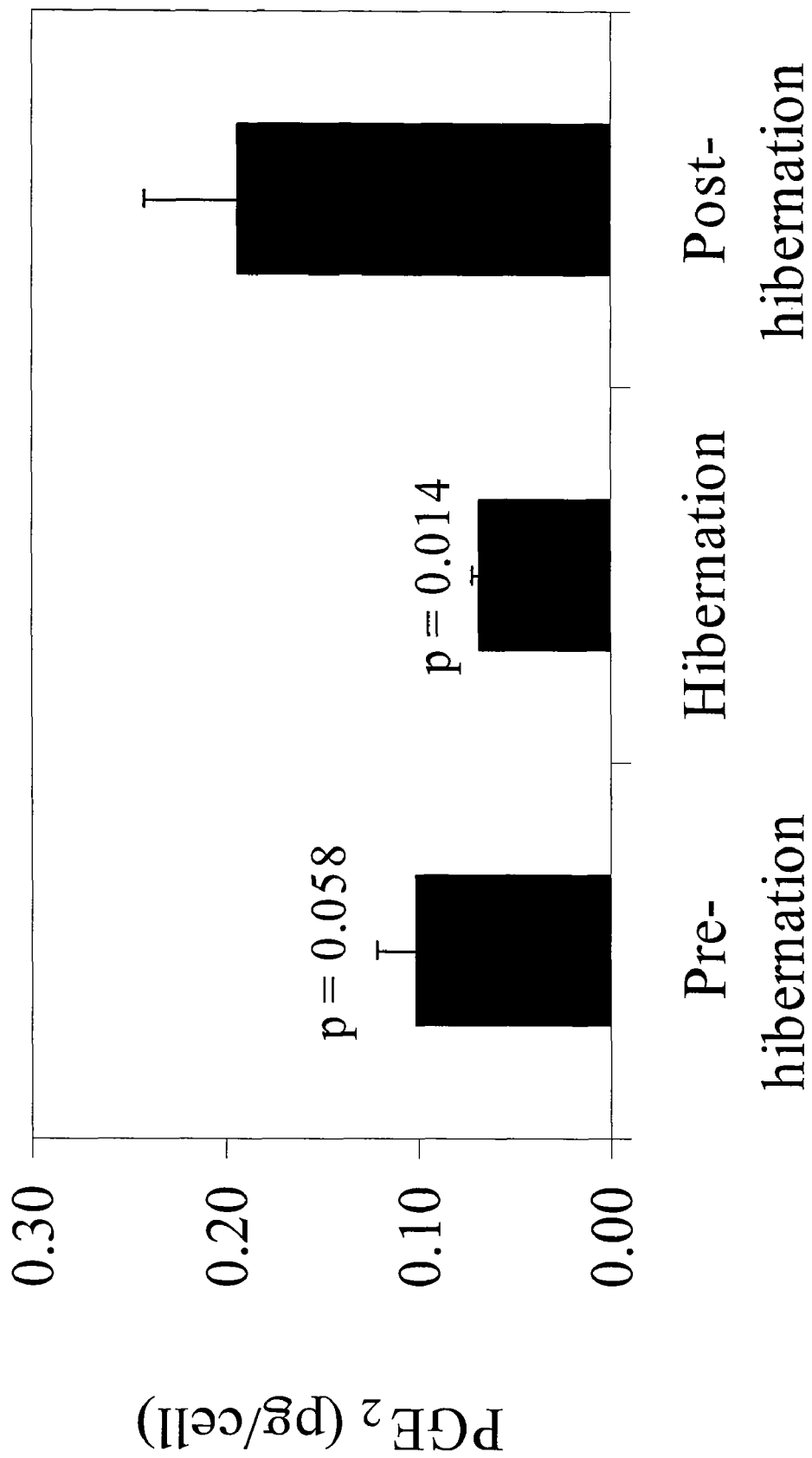
FIG. 4 shows that the amount of $PGE_2$ released by osteoblastic cells was greatest when the cells were treated with serum collected in the post-hibernation period.

The amount of $PGE_2$, released by osteoblastic cells treated with bear serum in vitro, was higher for treatment with post-hibernation serum compared to pre-hibernation serum (p=0.058) and hibernation serum (p=0.014) (FIG. 4). The $PGE_2$ release for cells treated with the hibernation serum was not significantly (p=0.48) different compared to the pre-hibernation serum. The seasonal changes in $PGE_2$ release showed trends similar to the seasonal changes in serum IGF-I. P-values are for comparisons with the post-hibernation value. Pre-hibernation and hibernation values were not different from each other (p=0.48).

Example 4

Culture in Bear Serum Decreases the Ratio of Gene Expression of Bax to Bcl-2 During Hibernation Blood serum samples were removed from 4 female black bears between 2004-2005 as described above. Sample dates

TABLE 1

| Mean Serum Metabolite Concentrations | | | | | | | | | |
|---|---|---|---|---|---|---|---|---|---|
| | Pre-hibernation | | | Hibernation | | | Post-hibernation | | |
| Osteocalcin (ng/ml) | 16.9[a] | (7.4) | [15] | 70.4[b] | (43.1) | [22] | 49.3[b] | (26.8) | [19] |
| Ionized calcium (mmol/L) | 0.709[a] | (.150) | [12] | 0.871[b] | (.093) | [10] | 0.960[b] | (.014) | [2] |
| PTH (pg/ml) | 14.6[a] | (4.5) | [6] | 25.3[a] | (27.3) | [14] | 41.4[b] | (20.2) | [9] |
| 25-OH D (nmol/ml) | 16.6 | (16.3) | [9] | 11.2 | (6.2) | [9] | 16.0 | (13.4) | [9] |
| Leptin (ng/ml) | 4.0[a] | (0.7) | [15] | 3.8[a] | (0.7) | [22] | 3.1[b] | (0.7) | [19] |
| IGF-I (ng/ml) | 387[a] | (88) | [15] | 209[b] | (52) | [22] | 594[c] | (207) | [19] |

Mean values are given in bold, standard deviations in parentheses, and sample sizes in brackets. For a given metabolite, values with the same superscript are not significantly (p < 0.05) different. 25-OH D did not show significant seasonal differences.

encompassed a pre-hibernation active period, a hibernation disuse period, and a post-hibernation remobilization period. MC-3T3 osteoblastic cells were cultured for 24 hours in media containing 10% bear serum, after which total RNA was isolated using a BioRad AquaPure RNA Isolation Kit (#732-6370, Bio-Rad Laboratories, Hercules, Calif.). To generate cDNA, reverse transcription was performed using Superscript II reverse transcriptase (Invitrogen, Carlsbad, Calif.), and 0.5 µg Oligo(dT) 12-18 primer at 42° C. for 20 minutes, 50° C. for 10 minutes and 42° C. for 1 hour in a gradient thermocycler (Mastercycler gradient, Eppendorf, Westbury, N.Y.). Primers for the pro-apoptotic protein Bax and the anti-apoptotic protein Bcl-2 were designed using PrimerQuest software (Integrated DNA Technologies, Coralville, Iowa) and the NCBI gene bank sequences. Semi-quantitative PCR was performed using RedTaq and a protocol consisting of 94° C. for 2 minutes, cycles of 94° C. for 30 seconds, 69.5° C. for 30 sec and 72° C. for 1 minute, and a final extension at 72° C. for 5 minutes. Band intensity was quantified using the ImageJ software package (National Institutes of Health, Bethesda, Md.) and normalized to the expression of three housekeeping genes (Gapdh, β-actin, cyclophillin).

ANOVA with Fisher's Protected Least Significant Difference (PLSD) post-hoc test was used to compare the ratio of Bax to Bcl-2 for the three seasons (pre-hibernation, hibernation, post-hibernation). Though it did not achieve statistical significance ($p=0.300$), the Bax/Bcl-2 ratio decreased by approximately 42% during hibernation relative to pre-hibernation. The lack of statistical significance was likely related to the small sample size (n=2 for each season). These data suggest that serum from hibernating bears contains a biological molecule that decreases osteoblast apoptosis. Since endogenous PTH and the bone formation marker osteocalcin both increase during hibernation (Donahue et al., 2006; J. Exp. Biol., 209, 1630-8), it is possible that endogenous bear PTH causes a decrease in osteoblast apoptosis during hibernation, which in turn increases bone formation.

Example 5

Comparison of Effects of Black Bear vs. Human PTH 1-84 or Subfragments Thereof on cAMP in Bone Cell Lines Full-length recombinant black bear PTH (residues 1-84) is produced and its effects on levels of cyclic adenosine monophosphate (cAMP) concentration in bone cell lines (MC-3T3 osteoblastic cells and MLO-Y4 osteocytic cells) are investigated and compared to results obtained using recombinant human PTH 1-84. Equivalent experiments are conducted using subfragments of black bear and human PTH, the subfragments including amino acid residues 1-34, 1-36, 7-84, 11-84, and 41-52 of the full-length (1-84) mature protein. For some experiments, black bear and human PTH polypeptides are synthesized with solid-phase methods.

To determine the effect of various forms of recombinant black bear and human PTH polypeptides on cAMP levels in bone-forming cells, the cultured bone cells (MC-3T3 and MLO-Y4) are contacted for 10 or 30 minutes with human or black bear PTH full-length (i.e. amino acid residues 1-84) polypeptide or one of the above-listed subfragments. After the cell is contacted with the PTH polypeptide, cAMP concentration in the cell is measured using a competitive binding assay as described further below.

For all of the experiments using recombinant polypeptides, the lyophilized peptides are reconstituted to 100 uM stock concentrations in 1 mM acetic acid, and diluted to 10 uM working stock concentrations before use.

Cell Culture

MC-3T3 subclone 14 cells (ATCC, CRL-2594) and MLO-Y4 cells (obtained from L. F. Bonewald, University of Missouri, Kansas City, Mo.) are maintained in alpha-minimum essential media, 1% penicillin/streptomycin, and 10% serum (MC-3T3: 10% fetal bovine serum (FBS), MLO-Y4: 5% FBS and 5% bovine calf serum), at 37° C. in 5% $CO_2$. All procedures described herein are repeated with independent cell cultures such that n=6 for all treatment combinations in each assay.

Effects of PTH Treatment on Intracellular cAMP Activity

MC-3T3 and MLO-Y4 cells are seeded at appropriate densities (MC-3T3: 50,000 cells/$cm^2$, MLO-Y4 15,000 cells/$cm^2$) in 6-well plates. Cells are cultured overnight to reach optimal confluence. The culture media is then aspirated and replaced with media containing either 10% serum+vehicle (1 mM acetic acid) or 10% serum+100 nM PTH (human or bear 1-84, or a subfragment thereof. Cells are cultured under these conditions for 10 or 30 minutes (Carter, P. H. et al., 1999, J. Biol. Chem. 274 (45), 31955-60; Chen, X. et al., 2002, Am. J. Physiol. Cell Physiol. 283 (5), C1432-40; Schiller, P. C. et al., 1999, J. Bone Miner. Res. 14 (9), 1504-12). Following culture, the cells are trypsinized, centrifuged, and resuspended in lysis buffer. The suspension is incubated for 10 minutes and centrifuged to separate cellular debris. The supernatant from the cell lysate (following a 2-fold dilution) is assayed for cAMP concentration using a competitive binding assay (Cyclic AMP Assay #KGE002, R&D Systems, Minneapolis, Minn.).

With each of the polypeptides tested, there is an increase in cellular cAMP levels in response to the black bear PTH-based polypeptide.

Example 6

Comparison of Effects of Black Bear vs. Human PTH 1-84 or Subfragments Thereof on Apoptosis in Bone Cell Lines Full-length recombinant black bear PTH (residues 1-84) is produced and its effects on apoptosis in bone cell lines (MC-3T3 osteoblastic cells and MLO-Y4 osteocytic cells) are investigated and are compared to results obtained using recombinant human PTH 1-84. Equivalent experiments are conducted using subfragments of black bear and human PTH, the subfragments including amino acid residues 1-34, 1-36, 7-84, 11-84, and 41-52 of the full-length (1-84) mature protein. For some experiments, black bear and human PTH polypeptides are synthesized with solid-phase methods.

To determine the relative ability of black bear and human PTH to prevent osteoblast and osteocyte apoptosis (under pro-apoptotic conditions), cells are incubated with human or black bear PTH 1-84, or one of the subfragments listed above, for one hour. Afterwards, cells are treated for 6 hours with dexamethasone to induce apoptosis. Apoptosis is quantified with an ELISA, as described further below.

For all of the experiments using recombinant polypeptides, the lyophilized peptides are reconstituted to 100 uM stock concentrations in 1 mM acetic acid, and diluted to 10 uM working stock concentrations before use.

Additional experiments are performed with MC-3T3 cells using either 0.1% or 10% FBS. Additional experiments with less (0.1%) than the normal (10%) amount of FBS are run and the results are analyzed to determine whether there is a significantly different response between experiments that are run with normal or lower levels of serum. In the experiments reported in this Example, the results are not affected by the amount of FBS that is used. Apoptosis protection studies show that each of the polypeptides tested reduces or prevents apoptosis in MC-3T3 cells.

Cell Culture

MC-3T3 subclone 14 cells (ATCC, CRL-2594) and MLO-Y4 cells (obtained from L. F. Bonewald, University of Missouri, Kansas City, Mo.) are maintained in alpha-minimum essential media, 1% penicillin/streptomycin, and 10% serum (MC-3T3: 10% fetal bovine serum (FBS), MLO-Y4: 5% FBS and 5% bovine calf serum), at 37° C. in 5% $CO_2$. All procedures described herein are repeated with independent cell cultures such that n=6 for all treatment combinations in each assay.

Effects of PTH Treatment on Apoptosis

MC-3T3 cells are seeded at 50,000 cells/cm$^2$, and MLO-Y4 cells are seeded at 15,000 cells/cm$^2$ in 6-well plates and cultured overnight to reach optimal confluence. The culture media is aspirated and replaced with media containing either 10% serum+vehicle (1 mM acetic acid) or 10% serum+100 nM PTH (human or bear 1-84, or a subfragment thereof). After a one-hour incubation (Jilka et al., 1999; J. Clin. Invest., 104, 439-46), 10 µM dexamethasone or its vehicle (DMSO) is added to each well and cells are incubated for 6 hours (Bellido, T. et al., 2003, J. Biol. Chem. 278(50), 50259-72; Jilka et al., 1999, J. Clin. Invest., 104, 439-46). The PTH polypeptide or vehicle is left in situ during apoptosis induction because the suppression of apoptosis by PTH is self-limiting (Bellido et al., 2003). After 6 hours, cells are trypsinized, centrifuged, resuspended, and counted using a hemocytometer. 50,000 cells are removed from the suspension and placed into lysis buffer. The lysate supernatant (following centrifugation) is removed for analysis and stored at −20° C.

Apoptosis is quantified from the lysate supernatant with an ELISA (Cell Death Detection ELISA, #1544675, Roche Applied Science, Indianapolis, Ind.). This assay detects mono- and oligonucleosomes from fragmented cellular DNA in the cytoplasmic fraction of cell lysates, and therefore provides a good measure of the early and middle stages of apoptosis. Briefly, samples are diluted in buffer solution and added to microplate wells coated with an anti-histone mouse monoclonal (clone H11-4) antibody. Lysate supernatant from the vehicle-treated cells serves as a negative control. Optical densities are measured at 405 nm following the addition of a peroxidase-conjugated anti-DNA mouse monoclonal (clone MCA-33) antibody, and the amount of apoptosis in each sample is determined relative to its corresponding negative control. All samples are assayed in duplicate.

Each of the polypeptides tested decreased apoptosis of the cells (under pro-apoptotic conditions).

Example 7

Comparison of Effects of Black Bear vs. Human PTH 1-84 or Subfragments Thereof on Gene Expression in Bone Cell Lines Full-length recombinant black bear PTH (residues 1-84) is produced and its effects on levels of gene expression in bone cell lines (MC-3T3 osteoblastic cells and MLO-Y4 osteocytic cells) are investigated and are compared to results obtained using recombinant human PTH 1-84. Equivalent experiments are conducted using subfragments of black bear and human PTH, the subfragments including amino acid residues 1-34, 1-36, 7-84, 11-84, and 41-52 of the full-length (1-84) mature protein. For some experiments, black bear and human PTH polypeptides are synthesized with solid-phase methods.

To determine the effect of black bear and human PTH on regulation of bone matrix, transcriptional regulatory, anti-apoptosis (Bcl-2) genes, and the pro-apoptosis gene Bax, cells are cultured for 1 or 3 hours with human or bear PTH 1-84 or a subfragment. Gene expression is quantified with real-time PCR.

For all of the experiments using recombinant polypeptides, the lyophilized peptides are reconstituted to 100 uM stock concentrations in 1 mM acetic acid, and diluted to 10 uM working stock concentrations before use.

Additional experiments are performed with MC-3T3 cells using either 0.1% or 10% FBS. Additional experiments with less (0.1%) than the normal (10%) amount of FBS are run and the results are analyzed to determine whether there is a significantly different response between experiments that are run with normal or lower levels of serum. In the experiments reported in this Example, the results are not affected by the amount of FBS that is used. Real-time PCR is used to assess gene expression levels at 1- and 3-hour time points following addition of the polypeptide, showing in particular that black bear PTH 1-34 upregulates gene expression in MC-3T3 cells.

Cell Culture

MC-3T3 subclone 14 cells (ATCC, CRL-2594) and MLO-Y4 cells (obtained from L. F. Bonewald, University of Missouri, Kansas City, Mo.) are maintained in alpha-minimum essential media, 1% penicillin/streptomycin, and 10% serum (MC-3T3: 10% fetal bovine serum (FBS), MLO-Y4: 5% FBS and 5% bovine calf serum), at 37° C. in 5% $CO_2$. All procedures described herein are repeated with independent cell cultures such that n=6 for all treatment combinations in each assay.

Effects of PTH Treatment on Gene Expression

MC-3T3 cells are seeded at a density of 50,000 cells/cm$^2$, and MLO-Y4 cells are seeded at a density of 15,000 cells/cm$^2$ in 6-well plates and cultured overnight to reach optimal confluence. The culture media are aspirated and replaced with media containing either 10% serum+vehicle (1 mM acetic acid) or 10% serum+100 nM PTH (human or bear 1-84, or a subfragment as listed above). Cells are cultured under these conditions for 1 or 3 hours; these time points correspond with PTH-induced upregulation of c-fos and osteocalcin (Jiang et al., 2004, J. Biol. Chem., 279, 5329-37; Chen et al., 2002). Total RNA is isolated using the SV Total RNA Isolation System (Promega, Madison, Wis.).

Reverse transcription to generate cDNA is performed using Superscript II reverse transcriptase (Invitrogen, Carlsbad, Calif.), and 0.5 µg Oligo(dT) 12-18 primer at 42° C. for 20 minutes, 50° C. for 10 minutes and 42° C. for 1 hour in a gradient thermocycler (Mastercycler gradient, Eppendorf, Westbury, N.Y.). Primers for all genes of interest (osteocalcin, osteopontin, type I collagen, c-fos, Runx2, Bax, Bcl-2, SOST) and housekeeping genes (Gapdh, β-actin, cyclophillin) are designed using PrimerQuest software (Integrated DNA Technologies, Coralville, Iowa) and the NCBI gene bank sequences, and the PCR conditions are optimized using RNA from MC-3T3 and MLO-Y4 cells. Real-time PCR is performed using the Mx3000P real-time PCR system (Stratagene, La Jolla, Calif.). The protocol involves a hot start at 95° C. for 10 minutes followed by 40 cycles of 95° C. for 30 seconds (denaturation), 69° C. for 1 minute (annealing) and 72° C. for 1 minute (extension). The exception to this protocol is for c-fos, which has an annealing temperature of 66° C. Each 25 µl reaction contains 1× Absolute™ qPCR SYBR® green mix (ABgene, Rochester, N.Y.), 0.1 µM forward and reverse primer, and 2.5 ng total RNA equivalent cDNA template. Gene expression is determined using the relative standard curve method normalized to the geometric mean of the three housekeeping genes. All samples are measured in duplicate, and any samples with a coefficient of variation (CV) greater than 10% are reanalyzed.

The polypeptides cause an upregulation of bone matrix, transcriptional regulatory, and transcriptional activator genes, and a decrease in the expression ratio of Bax/Bcl-2.

Example 8

Comparison of the Effects of Black Bear Serum from Different Seasons on Bone Cell Apoptosis and Gene Expression, and Correlation with Serum Levels of PTH and Osteocalcin Blood samples are collected from at least 3 different female black bears (*Ursus americanus pallas*) held in the Virginia Tech Center for Bear Research between 2004 and 2005. Serum from additional black bears is collected in subsequent years. The Virginia Polytechnic Institute and State University Animal Care Committee approved all bear handling protocols (#98-069-F&WS). The bears are anesthetized with a 2:1 mixture of ketamine (100·mg/ml):xylazine (100·mg/ml); the dosage is 1 cc of the mixture per 45.5 kg of body mass. Blood samples are drawn from the femoral vein while the bears are anesthetized, and the samples are transported to the laboratory in an ice-packed cooler. Immediately on return to the laboratory, the blood is centrifuged to isolate the serum, which is then frozen at −20° C. Blood samples are collected from each bear every 10 days from the beginning of October until the end of May. Hibernation begins in early January and ends in early April. Thus, the collection dates encompass an active pre-hibernation period, a disuse hibernation period, and an active post-hibernation remobilization period.

Aliquots of 10 μl of bear serum are assayed in duplicate for osteocalcin concentration by radioimmunoassay (Patterson-Allen et al., 1982; Anal. Biochem., 120, 1-7). This assay has previously been validated for bears (Donahue et al., 2006; J. Exp. Biol., 209, 1630-8). The antibody is guinea-pig anti-rat osteocalcin and tracer is $^{125}$I-labeled rat osteocalcin. Aliquots of 100 μl of bear serum are assayed in duplicate for PTH concentration (Donahue et al., 2006; J. Exp. Biol., 209, 1630-8) with an ELISA (Porcine Intact PTH ELISA Kit, #60-3305, Immutopics, Inc., San Clemente, Calif.). This assay binds the 39-84 region of PTH, and requires the 13-34 region of PTH to calorimetrically report PTH concentration. Thus, it provides a good measure of intact (1-84) PTH concentration as well as C-terminal subfragments 7-84 and 11-84. This ELISA has been shown to cross-react with bear PTH (Donahue et al., 2006; J. Exp. Biol., 209, 1630-8), and has 100% cross-reactivity with human PTH. To validate this assay for black bears, samples of culture media containing 10 nM recombinant black bear or human PTH 1-84 are assayed in duplicate. The known concentration of the PTH samples is compared to the measured concentration determined from the assay's standard curve. Any potential difference in cross-reactivity determined from these samples is used as a correction for endogenous black bear PTH concentration in the black bear serum samples.

The procedures described above for recombinant black bear PTH apoptosis and gene expression cell culture experiments with cultured bone-type cells are repeated, substituting the 100 nM recombinant PTH-containing media with culture media containing 10% black bear serum (from pre-hibernation, hibernation, or post-hibernation periods). The serum volumes are calculated following the PTH ELISA described above.

Serum from the hibernation and post-hibernation seasons causes a greater prevention of apoptosis compared to pre-hibernation serum, because PTH is higher during hibernation and post-hibernation than in pre-hibernation serum. Endogenous serum PTH concentrations are inversely related to apoptosis levels, in that higher serum PTH levels correspond to lower rates of apoptosis, i.e. serum PTH concentrations are negatively correlated with apoptosis levels.

Example 9

In Vivo Testing of Bear PTH

Black bear PTH, either full-length (1-84) or one of several functional subfragments thereof (1-34; 1-36; 7-84; 11-84; 41-52), are tested in vivo for anabolic stimulation of bone cells compared to an equivalent human PTH or subfragment. Each of the PTH polypeptides is synthesized and suspended in a pharmaceutically-appropriate carrier for subcutaneous injection. Full-length PTH or a functional fragment thereof, from either black bear or human, is administered to mice at a dose of 40 μg/kg body weight daily for 7 weeks. Black bear PTH or a functional fragments thereof cause greater increases in bone strength, mass, and mineral content than the equivalent human PTH polypeptide.

Example 10

Use of Bear PTH as Prophylactic Agent to Reduce or Prevent Bone Loss

Osteoporosis is induced in mice by hindlimb suspension (a disuse model of osteoporosis) and by ovariectomy (a postmenopausal model of osteoporosis). After the hindlimb suspension begins or the ovariectomy is completed, the mouse is given regular doses of black bear PTH or a functional fragment thereof. The mice treated with black bear PTH or functional fragments thereof show less bone loss than untreated mice.

Example 11

Bear and Human PTH 1-34 Both Upregulate Gene Expression of Osteocalcin, but Only Bear PTH 1-34 Decreases the Expression Ratio of Bax/Bcl-2

MC-3T3 cells were incubated in vehicle or 100 nM synthetic bear or human PTH 1-34 for 3 or 6 hours (n=2 or 4). Total RNA was isolated, and cDNA was generated with reverse transcription. Primers for the bone matrix proteins type I collagen and osteocalcin, the pro-apoptotic protein Bax, the anti-apoptotic protein Bcl-2, and the housekeeping genes Gapdh, β-actin, and cyclophillin were designed using PrimerQuest software (Integrated DNA Technologies, Coralville, Iowa). Real-time PCR was performed using the Mx3000P real-time PCR system (Stratagene, LaJolla, Calif.). All samples were measured in duplicate. Gene expression was determined using the relative standard curve method normalized to the geometric mean of the three housekeeping genes (Gapdh, β-actin, and cyclophillin). Apoptosis-related genes were analyzed as the expression ratio of Bax/Bcl-2, since a decrease in this ratio is associated with decreased apoptosis in vitro.

Figure 6:
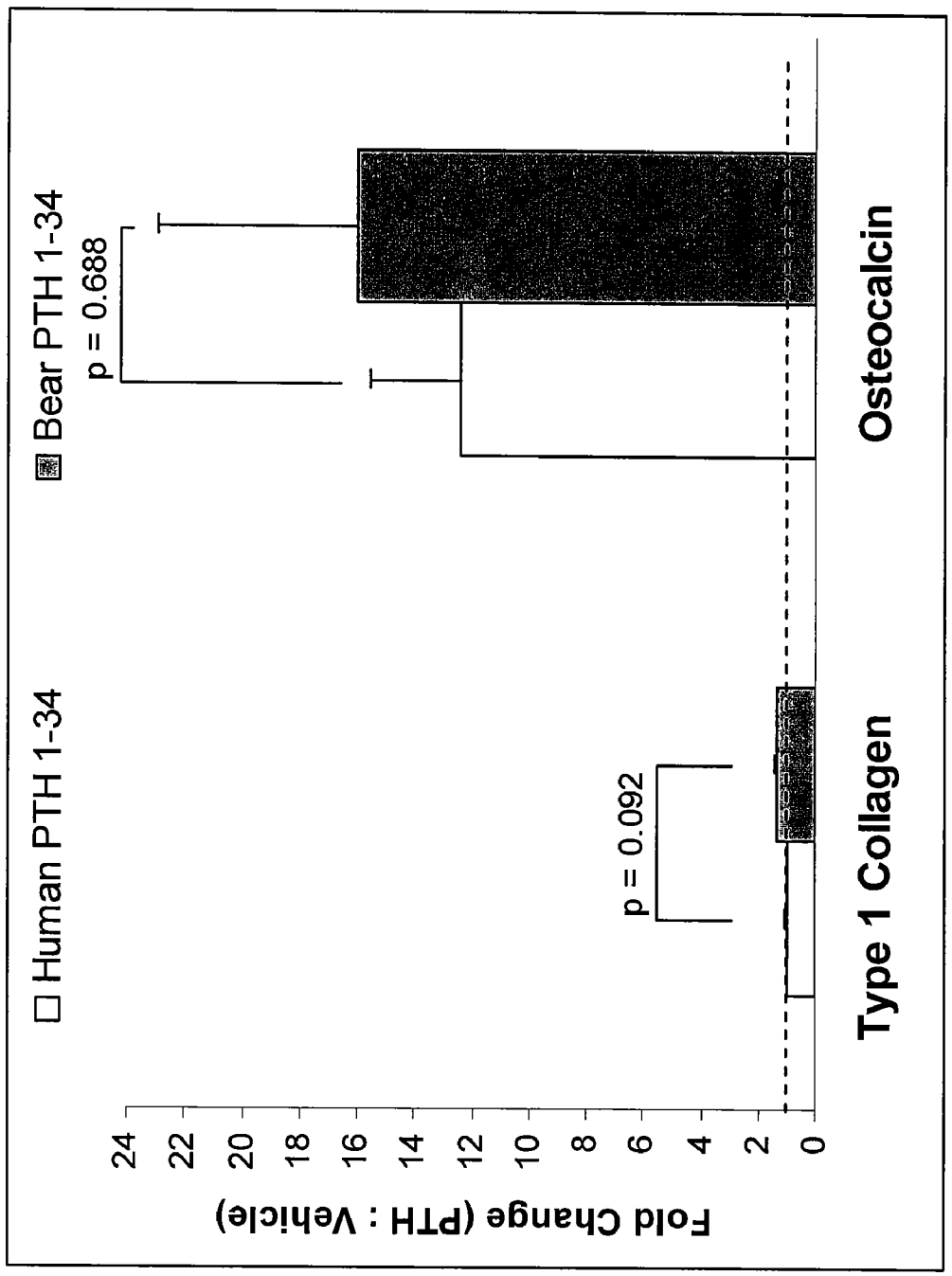
FIG. 6 shows that both human and black bear PTH 1-34 upregulate osteocalcin (n=2).

Culture in human or bear PTH 1-34 for 6 hours did not affect expression of type I collagen but substantially upregulated the expression of osteocalcin compared to the vehicle control (FIG. 6). There were no significant differences between human and bear PTH (p>0.09).

Culture in bear PTH 1-34 for 3 hours decreased the expression ratio of Bax/Bcl-2, suggesting decreased apoptosis, but culture in human PTH 1-34 for 3 hours increased the ratio, suggesting increased apoptosis (FIG. 7). The difference between bear and human PTH was statistically significant (p=0.047).

What is claimed is:

1. A method of increasing cAMP levels in a bone-forming cell comprising contacting the bone-forming cell with an effective amount of a polypeptide comprising amino acid residues 1-34 of SEQ ID NO: 2, wherein contacting the bone-forming cell with the polypeptide increases cAMP levels in the bone-forming cell, and wherein the bone-forming cell is in a human subject.

2. The method of claim 1, wherein the polypeptide comprises amino acid residues 1-36 of SEQ ID NO:2.

3. The method of claim 1, wherein the polypeptide comprises SEQ ID NO: 2.

4. A method of reducing apoptosis in a bone-forming cell comprising contacting the bone-forming cell with an effective amount of a polypeptide comprising amino acid residues 1-34 of SEQ ID NO: 2, wherein contacting the bone-forming cell with the polypeptide reduces apoptosis in the bone-forming cell, and wherein the bone-forming cell is in a human subject.

5. The method of claim 4, wherein the polypeptide comprises amino acid residues 1-36 of SEQ ID NO: 2.

6. The method of claim 4, wherein the polypeptide comprises SEQ ID NO: 2.

7. A method of decreasing the ratio of expression levels of Bax protein to Bcl-2 protein in a bone-forming cell comprising contacting the bone-forming cell with an effective amount of a polypeptide comprising amino acid residues 1-34 of SEQ ID NO: 2, wherein contacting the bone-forming cell with the polypeptide decreases the ratio of expression levels of Bax protein to Bcl-2 protein in the bone-forming cell, and wherein the bone-forming cell is in a human subject.

8. The method of claim 7, wherein the polypeptide comprises amino acid residues 1-36 of SEQ ID NO: 2.

9. The method of claim 7, wherein the polypeptide comprises SEQ ID NO: 2.

10. A method of increasing the expression level of one or more of a bone matrix protein, a transcriptional activator, or a transcriptional regulator in a bone-forming cell comprising contacting the bone-forming cell with an effective amount of a polypeptide comprising amino acid residues 1-34 of SEQ ID NO: 2, wherein contacting the bone-forming cell with the polypeptide increases the expression level of the bone matrix protein, the transcriptional activator, or the transcriptional regulator in the bone-forming cell, and wherein the bone-forming cell is in a human subject.

11. The method of claim 10, wherein polypeptide comprises amino acid residues 1-36 of SEQ ID NO: 2.

12. The method of claim 10, wherein the polypeptide comprises SEQ ID NO: 2.

13. A method of enhancing bone mineral density, increasing bone mass, decreasing bone loss, or reducing the incidence of bone fractures, or any combination thereof, in a human subject, comprising contacting a bone-forming cell in the human subject with an effective amount of a polypeptide comprising amino acid residues 1-34 of SEQ ID NO: 2, wherein contacting the bone-forming cell with the polypeptide enhances bone mineral density, increases bone mass, decreases bone loss, or reduces the incidence of bone fractures in the human subject.

14. The method of claim 13, wherein the human subject is a post-menopausal female human afflicted with osteoporosis.

15. The method of claim 13 further comprising administering vitamin D and calcium to the human subject.

16. The method of claim 13, wherein the polypeptide comprises amino acid residues 1-36 of SEQ ID NO: 2.

17. The method of claim 13, wherein the polypeptide comprises SEQ ID NO: 2.

18. A method of enhancing bone mineral density, increasing bone mass, decreasing bone loss, or reducing the incidence of bone fractures, or any combination thereof, in a human subject, comprising contacting a bone-forming cell in the human subject with an effective amount of a polypeptide comprising bear parathyroid hormone or a functional fragment thereof, wherein contacting the bone-forming cell with the polypeptide enhances bone mineral density, increases bone mass, decreases bone loss, or reduces the incidence of bone fractures in the human subject.

* * * * *

UNITED STATES PATENT AND TRADEMARK OFFICE
CERTIFICATE OF CORRECTION

| | | |
|---|---|---|
| PATENT NO. | : 7,994,129 B2 | Page 1 of 1 |
| APPLICATION NO. | : 11/559285 | |
| DATED | : August 9, 2011 | |
| INVENTOR(S) | : Seth W. Donahue | |

It is certified that error appears in the above-identified patent and that said Letters Patent is hereby corrected as shown below:

In the specification:

Col. 7, line 13, "down-regulates" should read --downregulates--.

Col. 11, line 59, "4'" should read --4°--.

Col. 16, line 20, insert --)-- after "thereof".

Col. 19, line 43, "calorimetrically" should read --colorimetrically--.

In the claims:

Col. 30, line 64, Claim 11 - insert --the-- after "wherein".

Signed and Sealed this
Tenth Day of April, 2012

David J. Kappos
*Director of the United States Patent and Trademark Office*

SEQUENCE LISTING

<160> NUMBER OF SEQ ID NOS: 13

<210> SEQ ID NO 1
<211> LENGTH: 255
<212> TYPE: DNA
<213> ORGANISM: Ursus americanus
<220> FEATURE:
<221> NAME/KEY: CDS
<222> LOCATION: (1)..(252)
<223> OTHER INFORMATION: cDNA encoding mature PTH polypeptide

<400> SEQUENCE: 1

```
tct gtg agc gag ata cag ttt atg cat aac ctg ggc aaa cat ctg agc      48
Ser Val Ser Glu Ile Gln Phe Met His Asn Leu Gly Lys His Leu Ser
1               5                   10                  15 tcc atg gag agg gtg gaa tgg ctg cgg aag aag ctg cag gac gtg cac      96
Ser Met Glu Arg Val Glu Trp Leu Arg Lys Lys Leu Gln Asp Val His
            20                  25                  30 aac ttt gtt gcc ctt gga gct cca aca gcg cac aga gat ggt ggt tcc     144
Asn Phe Val Ala Leu Gly Ala Pro Thr Ala His Arg Asp Gly Gly Ser
        35                  40                  45 cag agg ccc cag aaa aag gaa gac aat gtg ctg gtt gag aac cat caa     192
Gln Arg Pro Gln Lys Lys Glu Asp Asn Val Leu Val Glu Asn His Gln
    50                  55                  60 aaa agt ctc gga gaa gca gac aaa gct gat gtg gat gta tta acc aaa     240
Lys Ser Leu Gly Glu Ala Asp Lys Ala Asp Val Asp Val Leu Thr Lys
65                  70                  75                  80 tct aaa ccc caa tga                                                  255
Ser Lys Pro Gln
```

<210> SEQ ID NO 2
<211> LENGTH: 84
<212> TYPE: PRT
<213> ORGANISM: Ursus americanus

<400> SEQUENCE: 2

```
Ser Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp Val His
            20                  25                  30

Asn Phe Val Ala Leu Gly Ala Pro Thr Ala His Arg Asp Gly Gly Ser
        35                  40                  45

Gln Arg Pro Gln Lys Lys Glu Asp Asn Val Leu Val Glu Asn His Gln
    50                  55                  60

Lys Ser Leu Gly Glu Ala Asp Lys Ala Asp Val Asp Val Leu Thr Lys
65                  70                  75                  80

Ser Lys Pro Gln
```

<210> SEQ ID NO 3
<211> LENGTH: 348
<212> TYPE: DNA
<213> ORGANISM: Ursus americanus
<220> FEATURE:
<221> NAME/KEY: CDS
<222> LOCATION: (1)..(345)
<223> OTHER INFORMATION: cDNA encoding full-length PTH polypeptide

<400> SEQUENCE: 3

```
atg atg tct gcg aaa aac gtg gtt aaa gta atg att gtc atg ttt gca      48
Met Met Ser Ala Lys Asn Val Val Lys Val Met Ile Val Met Phe Ala
1               5                   10                  15
```

```
att tgt ttt ctt gca aaa tcg gat ggg aaa cct gtt aag aag aga tct     96
Ile Cys Phe Leu Ala Lys Ser Asp Gly Lys Pro Val Lys Lys Arg Ser
             20                  25                  30 gtg agc gag ata cag ttt atg cat aac ctg ggc aaa cat ctg agc tcc    144
Val Ser Glu Ile Gln Phe Met His Asn Leu Gly Lys His Leu Ser Ser
         35                  40                  45 atg gag agg gtg gaa tgg ctg cgg aag aag ctg cag gac gtg cac aac    192
Met Glu Arg Val Glu Trp Leu Arg Lys Lys Leu Gln Asp Val His Asn
     50                  55                  60 ttt gtt gcc ctt gga gct cca aca gcg cac aga gat ggt ggt tcc cag    240
Phe Val Ala Leu Gly Ala Pro Thr Ala His Arg Asp Gly Gly Ser Gln
65                  70                  75                  80 agg ccc cag aaa aag gaa gac aat gtg ctg gtt gag aac cat caa aaa    288
Arg Pro Gln Lys Lys Glu Asp Asn Val Leu Val Glu Asn His Gln Lys
                 85                  90                  95 agt ctc gga gaa gca gac aaa gct gat gtg gat gta tta acc aaa tct    336
Ser Leu Gly Glu Ala Asp Lys Ala Asp Val Asp Val Leu Thr Lys Ser
            100                 105                 110 aaa ccc caa tga                                                    348
Lys Pro Gln
        115

<210> SEQ ID NO 4
<211> LENGTH: 115
<212> TYPE: PRT
<213> ORGANISM: Ursus americanus

<400> SEQUENCE: 4

Met Met Ser Ala Lys Asn Val Val Lys Val Met Ile Val Met Phe Ala
1               5                   10                  15

Ile Cys Phe Leu Ala Lys Ser Asp Gly Lys Pro Val Lys Lys Arg Ser
             20                  25                  30

Val Ser Glu Ile Gln Phe Met His Asn Leu Gly Lys His Leu Ser Ser
         35                  40                  45

Met Glu Arg Val Glu Trp Leu Arg Lys Lys Leu Gln Asp Val His Asn
     50                  55                  60

Phe Val Ala Leu Gly Ala Pro Thr Ala His Arg Asp Gly Gly Ser Gln
65                  70                  75                  80

Arg Pro Gln Lys Lys Glu Asp Asn Val Leu Val Glu Asn His Gln Lys
                 85                  90                  95

Ser Leu Gly Glu Ala Asp Lys Ala Asp Val Asp Val Leu Thr Lys Ser
            100                 105                 110

Lys Pro Gln
        115

<210> SEQ ID NO 5
<211> LENGTH: 84
<212> TYPE: PRT
<213> ORGANISM: Macaca fascicularis

<400> SEQUENCE: 5

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
             20                  25                  30

Asn Phe Ile Ala Leu Gly Ala Pro Leu Ala Pro Arg Asp Ala Gly Ser
         35                  40                  45

Gln Arg Pro Arg Lys Lys Glu Asp Asn Ile Leu Val Glu Ser His Glu
     50                  55                  60
```

```
Lys Ser Leu Gly Glu Ala Asp Lys Ala Asp Val Asp Val Leu Thr Lys
 65                  70                  75                  80

Ala Lys Ser Gln

<210> SEQ ID NO 6
<211> LENGTH: 84
<212> TYPE: PRT
<213> ORGANISM: Homo sapiens

<400> SEQUENCE: 6

Ser Val Ser Glu Ile Gln Leu Met His Asn Leu Gly Lys His Leu Asn
  1               5                  10                  15

Ser Met Glu Arg Val Glu Trp Leu Arg Lys Leu Gln Asp Val His
                 20                  25                  30

Asn Phe Val Ala Leu Gly Ala Pro Leu Ala Pro Arg Asp Ala Gly Ser
             35                  40                  45

Gln Arg Pro Arg Lys Lys Glu Asp Asn Val Leu Val Glu Ser His Glu
         50                  55                  60

Lys Ser Leu Gly Glu Ala Asp Lys Ala Asp Val Asn Val Leu Thr Lys
 65                  70                  75                  80

Ala Lys Ser Gln

<210> SEQ ID NO 7
<211> LENGTH: 84
<212> TYPE: PRT
<213> ORGANISM: Equus caballus
<220> FEATURE:
<221> NAME/KEY: misc_feature
<222> LOCATION: (65)..(65)
<223> OTHER INFORMATION: Xaa can be any naturally occurring amino acid

<400> SEQUENCE: 7

Ser Val Ser Glu Ile Gln Leu Met His Asn Leu Gly Lys His Leu Asn
  1               5                  10                  15

Ser Val Glu Arg Val Glu Trp Leu Arg Lys Leu Gln Asp Val His
                 20                  25                  30

Asn Phe Ile Ala Leu Gly Ala Pro Ile Phe His Arg Asp Gly Gly Ser
             35                  40                  45

Gln Arg Pro Arg Lys Lys Glu Asp Asn Val Leu Ile Glu Ser His Gln
         50                  55                  60

Xaa Ser Leu Gly Glu Ala Asp Lys Ala Asp Val Asp Val Leu Ser Lys
 65                  70                  75                  80

Thr Lys Ser Gln

<210> SEQ ID NO 8
<211> LENGTH: 84
<212> TYPE: PRT
<213> ORGANISM: Canis lupus familiaris

<400> SEQUENCE: 8

Ser Val Ser Glu Ile Gln Phe Met His Asn Leu Gly Lys His Leu Ser
  1               5                  10                  15

Ser Met Glu Arg Val Glu Trp Leu Arg Lys Leu Gln Asp Val His
                 20                  25                  30

Asn Phe Val Ala Leu Gly Ala Pro Ile Ala His Arg Asp Gly Ser Ser
             35                  40                  45

Gln Arg Pro Leu Lys Lys Glu Asp Asn Val Leu Val Glu Ser Tyr Gln
         50                  55                  60
```

```
Lys Ser Leu Gly Glu Ala Asp Lys Ala Asp Val Asp Val Leu Thr Lys
 65                  70                  75                  80

Ala Lys Ser Gln
```

<210> SEQ ID NO 9
<211> LENGTH: 84
<212> TYPE: PRT
<213> ORGANISM: Felis catus

<400> SEQUENCE: 9

```
Ser Val Ser Glu Ile Gln Phe Met His Asn Leu Gly Lys His Leu Ser
 1               5                  10                  15

Ser Val Glu Arg Val Glu Trp Leu Arg Arg Lys Leu Gln Asp Val His
                20                  25                  30

Asn Phe Val Ala Leu Gly Ala Pro Ile Ala His Arg Asp Gly Gly Ser
            35                  40                  45

Gln Arg Pro Arg Lys Lys Glu Asp Asn Val Pro Ala Glu Asn His Gln
        50                  55                  60

Lys Ser Leu Gly Glu Ala Asp Lys Ala Asp Val Asp Val Leu Ile Lys
 65                  70                  75                  80

Ala Lys Ser Gln
```

<210> SEQ ID NO 10
<211> LENGTH: 84
<212> TYPE: PRT
<213> ORGANISM: Bos taurus

<400> SEQUENCE: 10

```
Ala Val Ser Glu Ile Gln Phe Met His Asn Leu Gly Lys His Leu Ser
 1               5                  10                  15

Ser Met Glu Arg Val Glu Trp Leu Arg Lys Lys Leu Gln Asp Val His
                20                  25                  30

Asn Phe Val Ala Leu Gly Ala Ser Ile Ala Tyr Arg Asp Gly Ser Ser
            35                  40                  45

Gln Arg Pro Arg Lys Lys Glu Asp Asn Val Leu Val Glu Ser His Gln
        50                  55                  60

Lys Ser Leu Gly Glu Ala Asp Lys Ala Asp Val Asp Val Leu Ile Lys
 65                  70                  75                  80

Ala Lys Pro Gln
```

<210> SEQ ID NO 11
<211> LENGTH: 84
<212> TYPE: PRT
<213> ORGANISM: Sus scrofa

<400> SEQUENCE: 11

```
Ser Val Ser Glu Ile Gln Leu Met His Asn Leu Gly Lys His Leu Ser
 1               5                  10                  15

Ser Leu Glu Arg Val Glu Trp Leu Arg Lys Lys Leu Gln Asp Val His
                20                  25                  30

Asn Phe Val Ala Leu Gly Ala Ser Ile Val His Arg Asp Gly Gly Ser
            35                  40                  45

Gln Arg Pro Arg Lys Lys Glu Asp Asn Val Leu Val Glu Ser His Gln
        50                  55                  60

Lys Ser Leu Gly Glu Ala Asp Lys Ala Ala Val Asp Val Leu Ile Lys
 65                  70                  75                  80

Ala Lys Pro Gln
```

```
<210> SEQ ID NO 12
<211> LENGTH: 84
<212> TYPE: PRT
<213> ORGANISM: Rattus norvegicus

<400> SEQUENCE: 12

Ala Val Ser Glu Ile Gln Leu Met His Asn Leu Gly Lys His Leu Ala
1               5                   10                  15

Ser Val Glu Arg Met Gln Trp Leu Arg Lys Lys Leu Gln Asp Val His
            20                  25                  30

Asn Phe Val Ser Leu Gly Val Gln Met Ala Ala Arg Glu Gly Ser Tyr
        35                  40                  45

Gln Arg Pro Thr Lys Lys Glu Glu Asn Val Leu Val Asp Gly Asn Ser
    50                  55                  60

Lys Ser Leu Gly Glu Gly Asp Lys Ala Asp Val Asp Val Leu Val Lys
65                  70                  75                  80

Ala Lys Ser Gln

<210> SEQ ID NO 13
<211> LENGTH: 84
<212> TYPE: PRT
<213> ORGANISM: Mus musculus

<400> SEQUENCE: 13

Ala Val Ser Glu Ile Gln Leu Met His Asn Leu Gly Lys His Leu Ala
1               5                   10                  15

Ser Met Glu Arg Met Gln Trp Leu Arg Arg Lys Leu Gln Asp Met His
            20                  25                  30

Asn Phe Val Ser Leu Gly Val Gln Met Ala Ala Arg Asp Gly Ser His
        35                  40                  45

Gln Lys Pro Thr Lys Lys Glu Glu Asn Val Leu Val Asp Gly Asn Pro
    50                  55                  60

Lys Ser Leu Gly Glu Gly Asp Lys Ala Asp Val Asp Val Leu Val Lys
65                  70                  75                  80

Ser Lys Ser Gln
```